US007762814B2

(12) United States Patent
van der Zel

(10) Patent No.: US 7,762,814 B2
(45) Date of Patent: Jul. 27, 2010

(54) METHOD OF MANUFACTURING AND INSTALLING A CERAMIC DENTAL IMPLANT WITH AN AESTHETIC IMPLANT ABUTMENT

(75) Inventor: Joseph Maria van der Zel, Hoorn (NL)

(73) Assignee: Oratio B.V., Hoorn (NL)

( * ) Notice: Subject to any disclaimer, the term of this patent is extended or adjusted under 35 U.S.C. 154(b) by 63 days.

(21) Appl. No.: 11/662,866

(22) PCT Filed: Sep. 14, 2004

(86) PCT No.: PCT/NL2004/000635
§ 371 (c)(1),
(2), (4) Date: Aug. 24, 2007

(87) PCT Pub. No.: WO2006/031096
PCT Pub. Date: Mar. 23, 2006

(65) Prior Publication Data
US 2009/0042167 A1 Feb. 12, 2009

(51) Int. Cl.
A61C 8/00 (2006.01)
(52) U.S. Cl. .................... 433/201.1; 433/213; 433/214
(58) Field of Classification Search ................ 433/213, 433/214, 223, 201.1; 264/16, 19, 20; 700/95
See application file for complete search history.

(56) References Cited
U.S. PATENT DOCUMENTS

| 5,192,325 A | 3/1993 | Kijima et al. |
| 5,989,029 A | 11/1999 | Osorio et al. |
| 6,280,193 B1 | 8/2001 | Peltier |
| 6,319,006 B1 | 11/2001 | Scherer et al. |

(Continued)

FOREIGN PATENT DOCUMENTS

BE    1011205 A3    6/1999

(Continued)

OTHER PUBLICATIONS

Massey, B.C. and Alder, M.D.; "Analyzing Implant Placement in the Posterior Maxilla"; Mar. 2002; J.Dent Res, Abstr 3554.

(Continued)

Primary Examiner—Cris L Rodriguez
Assistant Examiner—Eric Rosen
(74) Attorney, Agent, or Firm—The Webb Law Firm

(57) ABSTRACT

The present invention relates to a method for manufacturing a tooth prosthesis, for insertion in a jawbone, including an implant and an abutment on top of the implant. The method includes: defining a shape of the prosthesis and its location in the jawbone by using first data from a first CT scan image of the jawbone and second data from a second image of a gypsum cast, correlating first and second data by extracting from the first data first position reference data of a first reference in the first image, and from the second data second position reference data of a second reference in the second image, the second reference being identical to the first reference; performing a geometric transformation on the second data and/or the first data to have a coincidence of the second image with the first image and to combine the first and second data into composite scan data.

28 Claims, 11 Drawing Sheets

U.S. PATENT DOCUMENTS

| | | |
|---|---|---|
| 6,382,975 B1 | 5/2002 | Poirier |
| 2002/0097400 A1 | 7/2002 | Jung et al. |
| 2002/0160337 A1 | 10/2002 | Klein et al. |

FOREIGN PATENT DOCUMENTS

| | | |
|---|---|---|
| DE | 19530981 A1 | 2/1997 |
| EP | 1378735 A1 | 7/2004 |
| EP | 1449489 A1 | 8/2004 |
| WO | 9426200 A1 | 11/1994 |
| WO | 9528688 A1 | 10/1995 |
| WO | 0224098 A2 | 3/2002 |
| WO | 03028577 A2 | 4/2003 |
| WO | 03045268 A1 | 6/2003 |

OTHER PUBLICATIONS

T.M. Barker et al.; "Integration of 3-D Medical Imaging and Rapid Prototyping to Create Stereolithographic Models"; Australasian Physical & Engineering Sciences in Medicine, vol. 16, No. 2 (Jun. 1993): 79-85.

B. Swaelens et al.; "Medical Applications of Rapid Prototyping Techniques"; Proceedings of the Fourth International Conference on Rapid Prototyping, Dayton, Ohio, Jun. 14-17, 1993: 107-120.

Jef M. Van Der Zel et al; "The CICERO system for CAD/CAM fabrication of full-ceramic crowns"; J Prosth. Dent, Mar. 2001; 85:261-267.

Alma Dozic, DDS et al.; 2003, "The influence of porcelain layer thickness on the final shade of ceramic restorations"; Dec. 2003; J Prosth Dent; 90:563-70.

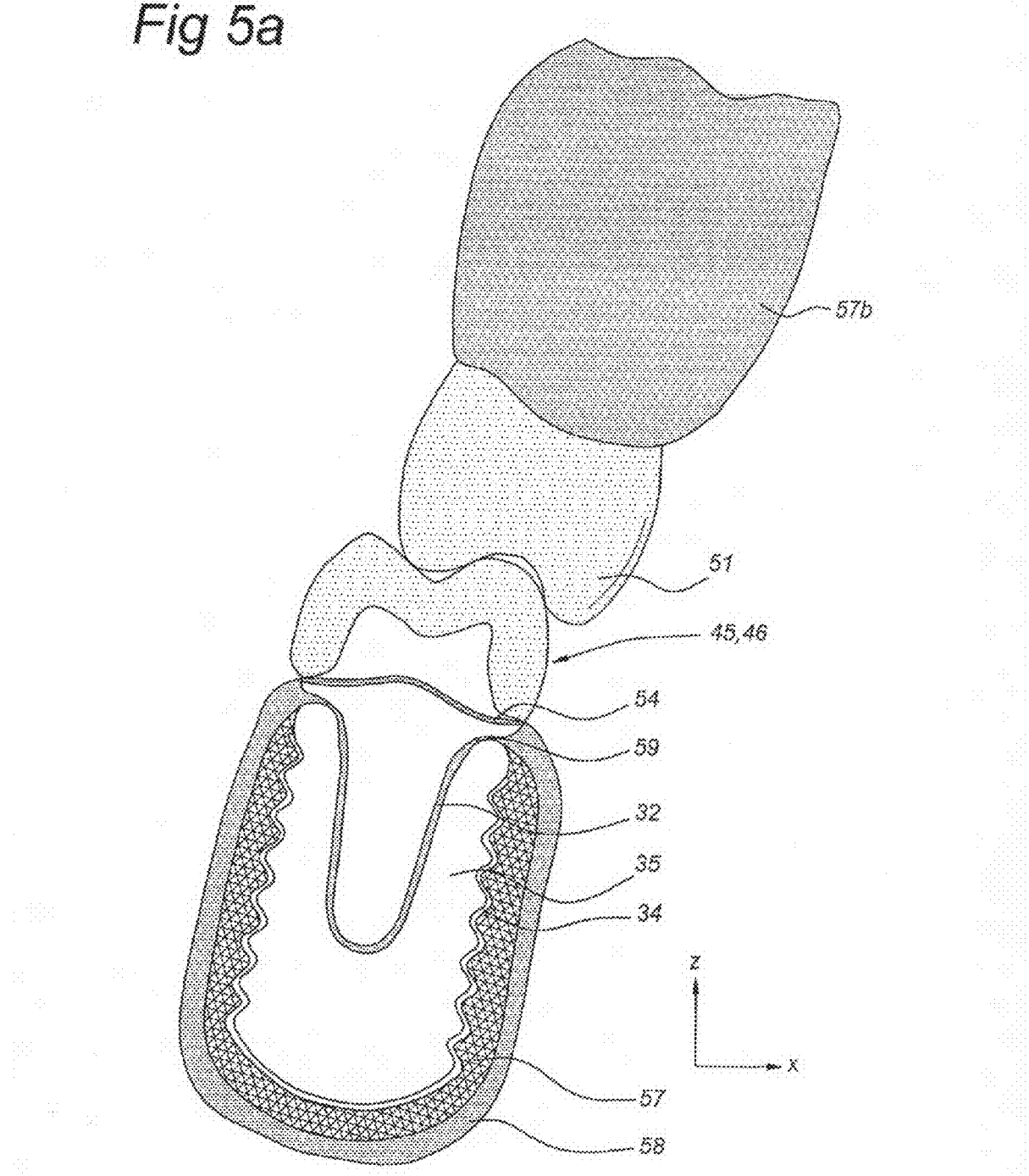

Fig 12 /1200

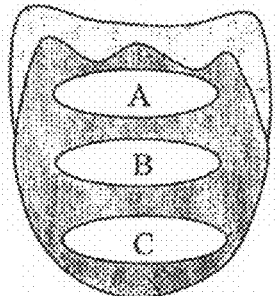

Measure color of corresponding tooth at
Level A: $L_A = L^*$, $a_A = a^*$, $b_A = b^*$.
Level B: $L_B = L^*$, $a_B = a^*$, $b_B = b^*$.
Level C: $L_C = L^*$, $a_C = a^*$, $b_C = b^*$.
— 1201

Calculate average color of A,B,C:
$L_M = (L_A + L_B + L_C)/3$
$a_M = (a_A + a_B + a_C)/3$
$b_M = (b_A + b_B + b_C)/3$
— 1202

Choose closest glass ceramic (g) color:
Color g: $L_g = L^*$, $a_g = a^*$, $b_g = b^*$, and
choose closest abutment core (ac) color:
Color c: $L_{ac} = L^*$, $a_{ac} = a^*$, $b_{ac} = b^*$,
while: $L_g > L_c$; $a_g > a_c$; $b_g > b_c$.
— 1203

Calculate glass ceramic distance, $D_{ijk}$:
For each level $x \in A,B,C$
Solve $D_{ijk}$ from::
$L^*$: $D_o \cdot L_x = D_{ijk,L} \cdot L_g + (D_o - D_{ijk,L}) \cdot L_{ac}$
$a^*$: $D_o \cdot a_x = D_{ijk,a} \cdot a_g + (D_o - D_{ijk,a}) \cdot a_{ac}$
$b^*$: $D_o \cdot b_x = D_{ijk,b} \cdot b_g + (D_o - D_{ijk,b}) \cdot b_{ac}$
— 1204

Calculate abutment core coordinates
— 1205

1206 — End

METHOD OF MANUFACTURING AND INSTALLING A CERAMIC DENTAL IMPLANT WITH AN AESTHETIC IMPLANT ABUTMENT

BACKGROUND OF THE INVENTION

1. Field of the Invention

The invention relates to a method for manufacturing a prosthesis for replacing at least one tooth, the prosthesis being arranged for insertion in a patient's jawbone, the prosthesis comprising an implant and an abutment in accordance with the preamble of claim 1. Also, the invention relates to a method for manufacturing a drill guide for use with the manufacturing of the prosthesis. Moreover, the present invention relates to a prosthesis comprising an implant and an abutment. Furthermore, the present invention relates to a drill guide for use in a patient's jaw bone without the need for a flapping operation. Also, the present invention relates to an impression tray for taking an impression of a denture of a patient. The present invention also relates to a computer system and a computer program product for manufacturing a prosthesis for replacing at least one tooth.

2. Description of the Related Art

Dental restorative systems seek to provide cosmetic and functional replacements for missing teeth. A dental restorative system that replaces a single tooth typically includes three components. These are the dental implant fixture, the abutment, and the crown. The dental implant fixture anchors the restorative system to the jawbone. The crown replicates the contour and appearance of the visible portion of the restorative system to match that of the natural dentition. Finally, the abutment connects the crown to the dental implant fixture. The abutment also holds the crown in proper alignment relative to the implant fixture, and absorbs the stress of chewing. A customized abutment should also match the size, shape and contour of the original tooth in order to provide the best possible appearance. In the prior art, the crown and the abutment consist of two separate parts. The abutment is screwed onto the implant and then the crown is cemented on the abutment, covering the screw of the abutment.

Standard methods for preparing dental restorative systems require considerable time, labor, and expense. Methods typically require that the patient make between six and ten visits to the dentist's office to complete installation of the restorative system. An oral surgeon or periodontist is required to surgically implant the dental implant fixture into the patient's jawbone. A general dentist or prosthodontist typically performs the measurement and fitting of the abutment and crown, and a technician typically sculpts the abutment and crown.

It is known in the art to secure dental prostheses using dental implants secured in the upper or lower jawbone. It is also known in the art to mount a framework or superstructure to a number of implants, the superstructure being used to evenly support a set of false teeth or denture prostheses. Accurate placement within the jawbone of the implants is a difficult task. In International Patent Application WO 94/26200, there is described an adjustable guiding device for positioning dental implants in which it is possible for the dental surgeon to adjust a drill axis for each implant before proceeding to use the guiding device or drill template to guide the surgeon's drill for the purposes of preparing the drill hole for the implant. The guiding device disclosed in WO 94/26200 helps the dental surgeon to decide on the drill axis after viewing radiographic images of the radio-opaque tubular drill guide superposed on the bone structure.

In the prior art, the oral surgeon typically has difficulty deciding on a drill axis for the implants since the ideal position for the implants should be decided with knowledge of the jawbone structure into which the implant is to be inserted, knowledge of the position within the jawbone structure of the nerve tissue, the gum surface and the required position and dimensions of the false teeth or dentures to be supported by the dental implant. In the conventional manner of selecting the implant axis, the dentist or dental surgeon simply makes a best guess in light of his knowledge of the patient. Of course, this leads, in certain cases, to imperfections in the dental prosthesis (see also: Massey, B. C.; Alder, M. E.: Analyzing Implant Placement in the Posterior Maxilla, J Dent Res, Abstr 3554, 2002).

The imperfections may relate to a lack of ideal support, an unfavorable angulation of an implant causing a weakness in the implant which may cause failure over time, or a visually perceptible defect in the appearance of the prosthesis.

In the conventional method for the construction of the superstructure, a physical model of the patient's gums and dental implant heads is prepared on which the superstructure is built manually using molding and other techniques known in the art. The craftsman or technician skilled at manufacturing such dental superstructures takes into consideration the size and shape of the desired dentures to be placed over the superstructure when crafting the same.

The procedure for manufacturing dental implant superstructures as known from the art is time-consuming and sometimes results in imperfect structures or defects in the visual appearance of the dentures to be placed over the superstructure.

U.S. Pat. No. 6,382,975 describes a method for manufacturing a dental implant drill guide and a dental implant superstructure in the form of a fixed dental prosthesis or an overdenture. The method comprises the manufacture of a scannographic scanning guide with reference spheres in specific positions. Disadvantageously, such a scannographic guide requires the manufacture of a jawbone model based on a physical model of the jaw.

U.S. Pat. No. 5,989,029 describes a method for the provision of a customized dental abutment which replicates a tooth being replaced. The dimensions of the abutment are determined by a computer algorithm that is capable of modifying standard tooth type models according to a series of measurements taken of the site of desired tooth replacement, i.e., the location for the replacement tooth. The method describes taking a series of measurements of the site of the desired tooth replacement, determining the type of tooth being replaced, and preparing or selecting a customized dental abutment based on the measurements and determination. The preparation or selection is made by modifying standard measurements for the type of tooth being replaced in conformity with the measurements taken of the site of desired tooth replacement. Disadvantageously, only discontinuous lines may be extracted from the model to modify a generic abutment parametrically and only so by selecting standard measurements that are entered.

WO 03/045268 describes a ceramic implant consisting of zirconia-based material and at least sections of the external surface of at least the anchor part are pre-treated using a subtractive method or are provided with a coating which supports ossification. Disadvantageously, the implant is treated after the material has reached its final density, which basically renders the material bio-chemically inert with respect to dental treatments.

In PCT/BE95/00033 a method is set fourth for making a perfected medical model on the basis of digital image information of a part of the body. The digital image information of a part of the body is converted, by means of what is called the rapid prototyping technique and thus with a processing unit and a rapid prototyping machine, into a basic model of which at least a part perfectly shows the positive or negative form of at least a portion of the part of the body. At least an artificial functional element with a useful function is added to the basic model as a function of the digital information and possibly as a function of additional external information. However, the models produced up to now, including three-dimensional images, do not take advantage of all the information contained in the image information. They form a perfect copy of the part of the body, but they do not contain any additional functional elements. Such models which are exact copies of real structures are for example produced from medical images with the technique disclosed in the article "Integration of 3-D medical imaging and rapid prototyping to create stereo lithographic models" from T. M. BARKER et al., published in "Australasian Physical & Engineering Sciences in Medicine", vol. 16, no. 2, June 1993, pages 79-85. Scanner data are transformed to a suitable format in a computer and the images are processed as a volume of so-called voxels (a volume pixel). The object is segmented prior to the meshing of the object surface and the creation of a stereo lithographic model. The obtained model cannot be used for registration, i.e., correlate to a position on the patient. Functional elements, such as an opening indicating the place and direction for drilling, can be added manually, but not as a function of the image information.

The information or data set from tomographic scanning, consisting of voxels and contours, can be converted into a set of contours per layer height. By using the grey scale value information in the image it is possible to increase resolution by working with sub-voxel resolution, as described by B. Swaelens and others in "Medical Applications of Rapid Prototyping Techniques", p. 107-120 of "Proceedings of the Fourth International Conference on Rapid Prototyping, Dayton, Ohio, Jun. 14-17, 1993". However, disadvantageously, this higher resolution is still insufficient to make a drilling guide fit perfectly on the mucosal surface or remaining dentition, even when the contours per layer are calculated to the layer height which is suitable for the rapid prototyping technique which is usually significantly lower than the scan distance. Disadvantageously, to obtain a sufficient higher resolution in the prior art would require higher X-ray doses and/or longer exposure times for a patient. Such additional exposure to high energy radiation may pose an increased risk for a patient health and is therefore clearly unwanted.

Moreover, PCT/BE95/00033 discloses that if an external element is added to the CT scan image this external element must be represented as voxels or contours as well, by means of cross section and shading algorithms. After an interactive processing of the image information (e.g., rotations, translations, etc.), it is necessary to return to the original CAD data for obtaining a higher accuracy of the inner surface of the drill guide. Clearly, such human-assisted processing must be elaborate and will require a large effort in processing time and costs.

SUMMARY OF THE INVENTION

It is an object of the present invention to provide a method of manufacturing an accurate dental implant drill guide for selected drill holes.

Also, it is an object of the present invention to provide a method of manufacturing a dental implant that can be used to receive and cement the extension of an abutment or abutment crown.

Moreover, it is an object of the present invention to provide a method of manufacturing an aesthetic implant abutment crown having static and dynamic contact with the adjacent and opposing teeth It is yet another object of the present invention to provide a manufacturing method which provide better accuracy and faster results than conventional methods.

It is yet another object of the present invention to provide a dental implant drill guide which is precise and easy to use such that use of such a dental implant drill guide for drilling of the dental implant holes does not require expert skill and knowledge beyond the skill of basic dental surgery, because it is not necessary to uncover big parts of the jawbone itself, known as "flap surgery".

It is furthermore an object of the present invention to provide tools for a dental surgeon or oral surgeon which will reduce the number of visits a patient needs to make to the dental surgeon or oral surgeon in order to have dental implants and a dental implant superstructure inserted.

It is yet another object of the present invention to reduce the X-ray radiation load for a patient during the several stages of the manufacturing of the implant and the crown.

It is yet another object of the present invention to provide a metal free zirconia implant with a coating which may facilitate a direct loading of the screw form implant due to a faster osseointegration process.

According to a first aspect of the invention, there is provided a method for manufacturing a prosthesis for replacing at least one tooth, the prosthesis being arranged for insertion in a patient's jawbone, the prosthesis comprising an implant and an abutment, the abutment and the implant being arranged for placing the abutment on the implant;

the method comprising the step of:

defining a shape of the prosthesis and a location in the jawbone for the prosthesis to be placed by using first image data of a first image taken by a CT scan of the patient's jawbone and by using second image data of a second image obtained from a gypsum cast, the gypsum cast taken from the patient's mouth, wherein the method comprises the step of correlating the first image data and the second image data by:

extracting from the first image data first reference marker data relating to a position of a first reference marker in the first image;

extracting from the second image data second reference marker data relating to a position of a second reference marker in the second image, the second reference marker being the same as the first reference marker;

performing a geometric transformation operation with use of the first and second reference marker data, on the second image data and/or the first image data to have a coincidence of the second image with the first image and to combine the first image data and the second image data into composite scan image data.

According to the second aspect of the invention, there is provided a method for manufacturing a prosthesis for replacing at least one tooth, the prosthesis being arranged for insertion in a patient's jawbone, the prosthesis comprising an implant and an abutment, the abutment and the implant being arranged for placing the abutment on the implant, wherein at least one of the abutment and the implant consists of a zirconia based ceramic.

According to the third aspect of the invention, there is provided a method for manufacturing a drill guide for use with the manufacturing of a prosthesis for replacing at least one tooth, the prosthesis being arranged for insertion in a patient's jawbone, the prosthesis comprising an implant and an abutment, the abutment and the implant being arranged for placing the abutment on the implant;

the method comprising the step of:

defining a shape of the prosthesis and a location in the jawbone for the prosthesis to be placed by using first image data of a first image taken by a CT scan of the patient's jawbone and by using second image data of a second image obtained from a gypsum cast, the gypsum cast taken from the patient's mouth, wherein the method comprises the step of correlating the first image data and the second image data by:

extracting from the first image data first reference marker data relating to a position of a first reference marker in the first image;

extracting from the second image data second reference marker data relating to a position of a second reference marker in the second image, the second reference marker being the same as the first reference marker;

performing a geometric transformation operation with use of the first and second reference marker data, on the second image data and/or the first image data to have a coincidence of the second image with the first image and to combine the first image data and the second image data into composite scan image data, and defining a shape for the drill guide from the first and second image data; the drill guide comprising a guiding hole and a drill tube, the drill tube being located in the guiding hole and arranged for holding, during use, a drill bit; the drill tube having an orientation for providing a drilling direction to be coinciding with an orientation for the implant and having a pre-calculated height for providing a depth transfer for a depth of the implant in the jawbone.

Moreover, the present invention relates to a method for manufacturing a prosthesis for replacing at least one tooth, the prosthesis being arranged for insertion in a patient's jawbone, the prosthesis comprising an implant and an abutment, the abutment and the implant being arranged for placing the abutment on the implant, wherein the method comprises the step of taking a CT Scan of the patient's jawbone to obtain first image data of a first image, a first reference marker being provided during the CT Scan;

taking a gypsum cast from the patient's mouth;

taking a scan image of the gypsum cast to obtain second image data of a second image, a second reference marker being provided during the taking of the scan of the second image;

defining a shape of the prosthesis and a location in the jawbone for the prosthesis to be placed by using the first image data of the first image taken by a CT scan of the patient's jawbone and by using the second image data of the second image obtained from the gypsum cast, the gypsum cast taken from the patient's mouth, correlating the first image data and the second image data by:

extracting from the first image data first reference marker data relating to a position of the first reference marker in the first image;

extracting from the second image data second reference marker data relating to a position of the second reference marker in the second image, the second reference marker being the same as the first reference marker;

performing a geometric transformation operation with use of the first and second reference marker data, on the second image data and/or the first image data to have a coincidence of the second image with the first image and to combine the first image data and the second image data into composite scan image data.

Also, the present invention relates to a prosthesis comprising an implant and an abutment, the abutment being arranged for placement on the implant, wherein the prosthesis is manufactured according to any one of the methods as described above.

Furthermore, the present invention relates to a drill guide comprising a guiding hole and a drill tube, the drill tube being located in the guiding hole and arranged for holding, during use, a drill bit; the drill tube having an orientation for providing a drilling direction to be coinciding with the orientation for the implant and having a pre-calculated height for providing a depth transfer for the depth of the implant in the jawbone, manufactured in accordance with the method as described above.

Also, the present invention relates to an impression tray for taking an impression of a denture of a patient, characterised in that the impression tray comprises an orientation device comprising reference spheres located at defined distances from each other, the impression tray is relatively translucent for CT scan radiation, and the reference spheres are relatively opaque for CT scan radiation.

In a still further aspect, the present invention relates to a computer system for manufacturing a prosthesis for replacing at least one tooth, the prosthesis being arranged for insertion in a patient's jawbone, the prosthesis comprising an implant and an abutment, the abutment and the implant being arranged for placing the abutment on the implant;

the computer system comprising a processing unit and memory, the memory being connected to the processing unit, and being arranged for carrying out the step of:

defining a shape of the prosthesis and a location in the jawbone for the prosthesis to be placed by using first image data of a first image taken by a CT scan of the patient's jawbone and by using second image data of a second image obtained from a gypsum cast, the gypsum cast taken from the patient's mouth, wherein the processing unit is arranged for carrying out the step of correlating the first image data and the second image data by:

extracting from the first image data first reference marker data relating to a position of a first reference marker in the first image;

extracting from the second image data second reference marker data relating to a position of a second reference marker in the second image, the second reference marker being the same as the first reference marker;

performing a geometric transformation operation with use of the first and second reference marker data, on the second image data and/or the first image data to have a coincidence of the second image with the first image and to combine the first image data and the second image data into composite scan image data.

In still another aspect, the present invention relates to a computer program product to be loaded by a computer system (1308) for manufacturing a prosthesis for replacing at least one tooth, the prosthesis being arranged for insertion in a patient's jawbone, the prosthesis comprising an implant and an abutment, the abutment and the implant being arranged for placing the abutment on the implant;

the computer system comprising a processing unit and memory, the memory being connected to the processing unit and being arranged for carrying out the step of:

defining a shape of the prosthesis and a location in the jawbone for the prosthesis to be placed by using first image data of a first image taken by a CT scan of the patient's jawbone and by using second image data of a second image obtained from a gypsum cast, the gypsum cast taken from the patient's mouth, and wherein the computer program product after being loaded allows the processing unit to carry out the step of correlating the first image data and the second image data by:

extracting from the first image data first reference marker data relating to a position of a first reference marker in the first image;

extracting from the second image data second reference marker data relating to a position of a second reference marker in the second image, the second reference marker being the same as the first reference marker;

performing a geometric transformation operation with use of the first and second reference marker data, on the second image data and/or the first image data to have a coincidence of the second image with the first image and to combine the first image data and the second image data into composite scan image data.

Also, in still another aspect the present invention relates to a computer program product to be loaded by a computer system for manufacturing a prosthesis for replacing at least one tooth, the prosthesis being arranged for insertion in a patient's jawbone, the prosthesis comprising an implant and an abutment, the abutment and the implant being arranged for placing the abutment on the implant;

the computer system comprising a processing unit and memory, the memory being connected to the processing unit, and being arranged for carrying out the step of:

providing a predetermined color for the abutment;

the predetermined color being obtained from color data measured by at least one measurement on a tooth to be replaced or on a neighbor element by a method for determining color;

the at least one measurement comprising measuring on a predetermined position on the tooth to be replaced or the neighbor element color values;

determining an average of the color values for each of the at least one measurement;

selecting a closest glass ceramic color for the cap of the abutment with glass ceramic color values;

selecting a closest abutment body color for the abutment body with abutment body color values, with the abutment body color values being smaller than the glass ceramic color values;

determining a glass ceramic thickness by solving a color expression model using the measured color values for the at least one measurement under assumption of a certain value of an opacity thickness, and calculating abutment body coordinates.

The computer system and computer program product(s) implement the method as described above. A medical image of the jawbone of a patient is obtained by using x-ray imaging, MRI or possibly nuclear imaging techniques to produce a three-dimensional computer graphics model which has a reference to the implant jaw surface and the registration bite impression surface of the opposing teeth.

The primary advantage of the invention is that the oral surgeon may select the optimum position for a dental implant using the three-dimensional computer graphics model of the jawbone including the implant jaw and the position of the opposing teeth. The method allows the surgeon to interactively select an optimal position for a drill hole to be made in the jawbone in accordance with the optimal position for the dental implant. The optimal drill hole position not only relates to the coordinates of the planned drill hole on the jawbone, but also on the orientation of the drill hole (drill hole axis) within the jaw. Upon installation of the implant in the jaw, the implant will take the orientation of the drill hole.

Next, the selection of the drill hole position using the computer graphics model is transmitted to a centralized production facility where a drill guide is manufactured by a stereo lithography manufacturing method (SLA).

While the model is three-dimensional, it may be convenient for the purposes of selecting the drill hole axis to use a two-dimensional representation of the jawbone and the opposing teeth, the two-dimensional view being displayed with a user controlled angle. Preferably, the dental surgeon will select the position for each implant drill hole, not only to position each implant in the optimum location within the jawbone, but also to result in a position that is optimal in the loading of the implants during use for example, chewing. Therefore, it is preferred to display, in addition to the three-dimensional computer graphics model of the jawbone, the opposite teeth in the proper spatial relationship with respect to the jawbone. This requires imaging the patient's opposite teeth, in addition to the jawbone, in such a way that all images are referenced with respect to one another to be integrated into the same three-dimensional computer graphics model.

Imaging of the implant jaw surface and the registration bite impression can be carried out by using laser camera imaging techniques known in the art. These images are preferably obtained by placing the implant jaw gypsum model in the scanning device and scan the model.

Then the implant jaw impression tray with the reference spheres is placed on top of the gypsum model and the spheres are scanned simultaneously with the gypsum model still clamped in the same position. Next, the impression tray is removed and the registration bite impression is placed on top of the gypsum model and scanned. Advantageously, the opposing teeth surface of the registration bite is now calibrated with the reference spheres, and merging with the CT scan with the same impression tray with the reference spheres in the mouth of the patient during the CT scan, can be executed with ease.

In the method of manufacturing the dental implant aesthetic abutment or abutment crown with an ellipsoidal conical extension, according to the invention, the actual dental implant position data is obtained preferably by making another CT scan to find the orientation of the internal ellipsoidal recess position in the implant. Preferably, the imprint is taken using the same drill guide according to the invention with the titanium inserts in place. In this manner, an visual check of the proper alignment of the drill sockets with the orientation of the radio-opaque zirconia implants is advantageously provided.

The ideal form of the aesthetic implant abutment is automatically designed using generic library models of the abutment with the standard conical extension for cementation into the implant recess, from a library taking into consideration the form of the designed theoretical crown contour and by subtracting a thickness of porcelain which is necessary to recreate the shade of the missing tooth.

Dental aesthetic abutment or abutment crowns of the present invention are customized to replicate a tooth being replaced. Geometric data are obtained by a hybrid scanning method. CT-scanning for implant planning and drill hole orientation of the drill guide and an optical scan of an gypsum cast of the impression of the implanted jaw and an impression of the antagonists (opposing teeth). By a special impression technique whereby calibrated reference spheres are fixed to the impression tray and which are scanned both by CT- and optical scanning, the data of all scans can be merged in the CT Scan Space. From the optical scan data the mucosa line around the implant site is extracted mathematically and the extracted line is used to shape the equator line of the abutment part.

The present invention also provides for the preparation of a dental implant and an aesthetic implant abutment or abutment crown in a manner that advantageously reduces the amount of time, labor and cost involved in dental restorative system installation.

In the present invention a combination of CT-scanning and optical scanning are used to design the implant position and the aesthetic abutment to be produced by an automated system in a centralized production facility, in fewer steps and with a minimal amount of handwork. During a first office visit by a patient, an impression of the patient's existing teeth is made with a special impression tray with calibrated reference spheres. Also, a registration bite impression is taken from the patient's mouth that replicates the antagonistic teeth in central occlusion.

Furthermore, a first CT scan is made with the special impression tray in position in the mouth of the patient. The dentist can now plan the implant drill holes with the end point and the gum level point indicating the position and the orientation of the specifically chosen implant. Because the antagonistic teeth information is available during this planning stage the dentist has a good control over the correct orientation with regard to the future loading of the implants by chewing forces exerted by the antagonistic dentition. The planning data are sent to a centralized production facility where a drill guide is produced by stereo lithography with the holes at the proper place.

During a second visit, the dental implant fixture is installed in the patient's jawbone using the drill guide. The drill guide has inserts of titanium with a diameter that is suitable for the drills used starting with a small diameter insert for the first pilot drill and depth and ending with an insert for the final diameter drill and depth.

After healing, a third visit is necessary to make a second CT scan with the special impression tray with the calibrated reference spheres attached in place in the patient's mouth, showing the orientation of the recess in the implant, so that the aesthetic abutment or abutment crown can be designed with the extension in the proper orientation. In a fourth visit the aesthetic abutment crown is cemented on the implant.

The standard procedure requires a much higher number of visits to the dentist's office for the patient and the labour of up to three different dental professionals. This time and labour adds to the high cost of undergoing a tooth replacement by this method. Accordingly, the present invention addresses a need for a reduction of time, labour and cost by presenting customized aesthetic abutment or abutment crowns, a directly loadable metal free ceramic implant and low radiation scanning methods, which is quicker and less costly than standard techniques.

By making the first CT scan of the bone and optical impressions of the impressions of the site of tooth replacement, a quicker and easier development of a implant with an aesthetic abutment or abutment crown becomes possible. Accordingly, the present invention allows for the design and construction of an implant with a cemented aesthetic implant abutment or abutment crown reconstructed and designed from scan data of that first CT scan.

The method according to the present invention comprises optical scanning of a study cast, previously made of the patient's mouth. This study cast serves as a model of the patient's mouth and shows the site of desired tooth replacement as well as the relation of such a replacement tooth to the surrounding teeth. Also an bite impression (a registration bite), made for example in a heavy body silicone material, is scanned to gain surface data of the antagonistic teeth.

Another aspect of the invention relates to selection of an implant from an inventory of such implants. The inventory is preferably a computer inventory. Measurements such as the diameter and length are used to select an implant model that is most appropriate for the patient at the location of implantation taking account of the quantity and quality of the bone and eventual risk structures such as for example the nervus maxillaris.

In a further aspect of the invention, a computer program is used for planning the ceramic bioactive implant and for designing a model of the customized aesthetic abutment or abutment crown based on the optical scanning data. The computer is arranged for carrying out a program capable of generating a model of the customized aesthetic abutment or abutment crown based on the particular tooth being replaced and on the reconstructed scan data.

The computer has access to a database containing a series of standard tooth shapes for each type of tooth. The standard shape for the particular type of tooth being replaced is then computationally modified and customized by a parametric deformation algorithm. To obtain an real-world object according to this customized model, the computer program is capable of generating a series of instructions for milling paths to be used in a milling machine for the automatic production of the aesthetic abutment or abutment crown.

The technician needs only to characterize the final crown by staining as necessary before the dentist will cement the crown into the implant in the patient's jaw by a suitable cement, for instance, Panavia F (Kuraray, Japan).

BRIEF DESCRIPTION OF THE DRAWINGS

For the purpose of teaching of the invention, preferred embodiments of the method and devices of the invention are described below. It will be appreciated by the person skilled in the art that other alternative and equivalent embodiments of the invention can be conceived and reduced to practice without departing form the true spirit of the invention, the scope of the invention being limited only by the appended claims.

FIG. 5a shows a sectional view of the implant with the cemented aesthetic implant abutment crown in place in occlusal contact with the opposing teeth.

FIG. 12 shows the flow of the computer calculated core coordinates for determining a colour of the replacement tooth.

DETAILED DESCRIPTION OF THE INVENTION

Figure 1:
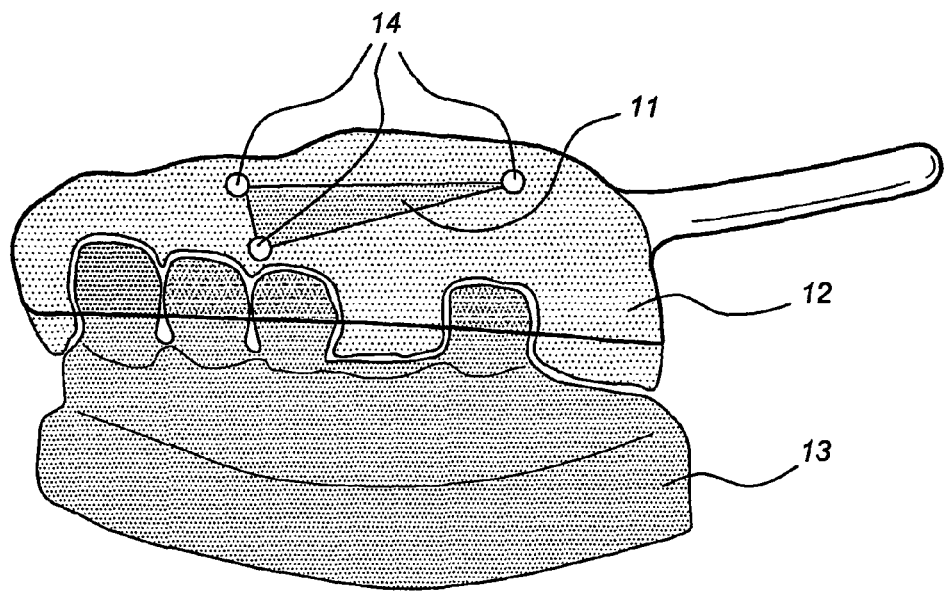
FIG. 1 shows a schematic view of the special impression tray with reference spheres on a gypsum cast of a dentures impression.

The present invention relates to methods and materials for use in dental restorative systems. A dental restorative system replaces a tooth in a patient's mouth. A dental restorative system is shown in FIG. 5*a* and comprises a dental implant, and an aesthetic abutment or abutment crown, cemented on the implant in the mouth of a patient at the site of desired tooth replacement. The dental implant fixture anchors the other components of the dental system in proper position and alignment with respect to the natural dentition. The dental system also includes an aesthetic abutment crown, which is installed in the dental implant fixture. The abutment crown is the visible portion of the restorative system, so it must be contoured and shaped to look like a natural tooth. The underlying abutment should also be fabricated to match the size, shape and contour of the replaced tooth.

More specifically, present invention provides bioactive ceramic implants with customized aesthetic abutment or abutment crowns for use in dental restorative systems and methods of production of such implants and aesthetic abutments or abutment crowns. An aesthetic abutment or abutment crown of the invention is fabricated based on the reconstruction of data derived from CT-scanning of the bone structure and optical scanning of impressions.

In methods of the invention, a dentist is assisted by a suitable computer system equipped with a computer program product in accordance with the present invention to select in the CT Scan Space an implant drill position with respect to their orientation to an implanted dental fixture. The reconstructed CT scan of the bone and the optical scan of the antagonists are used to place a dental fixture, such as incorporated in this invention, which is to be implanted in a bore hole made in a patient's jaw at the site of desired tooth replacement.

The implant site is surgically prepared by drilling into the jawbone after the gingival tissue surrounding the point of insertion of the implant has been retracted. An implant fixture may comprise a male hexagonal interface at its exposed end, as well as a hollow bore, which is open from the exposed end of the fixture and extends into the fixture recess.

An impression is preferably made through the use of an impression tray made of material that does not absorb X-ray radiation, such as plastic and is provided with at least three calibrated reference spheres that are radio-opaque, for instance zirconia After the study cast and impression are completed, the method according to the invention provides for the scanning of the cast and an impression of the antagonist teeth obtained by a registration bite in the patient's mouth. Then the impression tray is placed on the gypsum cast and the calibrated reference spheres are optically scanned in that position on the gypsum cast.

Both impression and CT scan provide images of the patient's denture and jawbone. These images are needed as information for the placement of the replacing prosthesis comprising implant and abutment (crown), its shape and also for the manufacturing of the prosthesis based on its shape.

An impression or CT scan of the positional and rotational alignment of the dental fixture with respect to the natural dentition must then be taken. The impression or CT scan ensures that the abutment and crown will have the proper alignment to fit into occlusion against opposing antagonistic teeth and the neighboring teeth.

From the scan of the gypsum cast of the implanted jaw the computer extracts the implant surrounding gum line for the design of the "mucosa-line" feature of the aesthetic abutment or abutment crown.

For the design of the translucent glass ceramic contour of the crown the operator selects a proper generic library stored within a database.

An abutment is customized by not only entering measurements into an algorithm but also by taken into account the complete gingival contour that was derived by reconstruction of the preparation line from the optical scan data. The design data include the generation of a model of the customized abutment based on a generic library model that can be deformed parametrically to give a functional and aesthetic restoration of the lost element.

The computer is programmed to fit the generic model of the customized abutment with crown to the adjacent element and the antagonistic teeth. The computer is pre-programmed to contain a series of library abutments and crowns for each type of tooth. The standard generic library tooth is modified to fit in the mouth. Once the surface data of the gingiva are reconstructed to a surface the implant fixture is placed in the correct position on the computer screen. The abutment is interactively manipulated to include the mesial-distal angle of the site of tooth replacement, the facial-lingual angle of the site, the rotational axis of the fixture, the gumline to marginal line of a dental implant fixture implanted in a patients mouth. The specific tooth being replaced (e.g., lateral incisor, first bicuspid, etc.) is also determined from its position in the mouth. Based on this computer reconstruction a customized abutment crown including veneering is fabricated. Other scanned data may be used to guide the manufacture of a customized dental abutment with crown, such as the occlusal surface obtained by an optical scan of the registration bite impression.

The abutment tooth shape is then taken from that database in the computer and adjusted and deformed to fit exactly with its outer contour in the space between adjacent and opposing teeth (i.e., the site of desired tooth replacement). The bottom part of the generic abutment tooth corresponds with the standardized opening in the zirconia implant, whatever its length or diameter.

Mesial and distal contacts if present are determined to design the "equator"-feature of the translucent porcelain contour of the abutment tooth. In a preferred embodiment, the surface of the antagonists obtained by the scan of the registration bite is used to bring the contour of the translucent porcelain layer of the aesthetic abutment or abutment crown in occlusal contact with the antagonist. After the computer calculates a simulated chewing movement eventual clenching intrusion can be corrected in the occlusal plane of the crown. The deformation is controlled by a parametric modelling algorithm so that the generic tooth maintains its proper tooth model. For multi-element bridges this operation can be performed for each element.

From the data obtained by the computer-aided design as described above, the prosthesis is manufactured. According to the present invention, the prosthesis is sintered from sintering material comprising at least a zirconia based compound.

A customized aesthetic dental abutment or abutment crown so fabricated is then sent to the dental practitioner for installation into the dental implant fixture implanted into the patient's jawbone. After the site of the implanted dental fixture has healed, the customized dental abutment of the invention is secured in place in the dental implant fixture by, for example, cementing it into place in the dental implant fixture. As a cement a glass-ionomer cement may be used for example, Panavia F from Kuraray of Japan. The use of a healing abutment is not required.

After placement on the implant, the aesthetic abutment or abutment crown may require some minor corrections at the mesial and distal contacts and in the occlusal plane. The dental practitioner can do this in the usual way at the try-in before cementing the aesthetic abutment or abutment crown permanently.

The aesthetic abutment or abutment crown is typically required to approximate the shape and color of the natural dentition. According to the present invention, a dental restoration can be performed without the high number of office visits required by standard methods, and without the amount of time, cost and labor involved in standard methods. Additional aspects and advantages of the invention are apparent upon consideration of the foregoing.

It is quite clear that the bioceramics discipline is evolving into an important field of study with great implications for our future health and well being. There is an increased need for the development of load-bearing "smart" biomaterials eliciting predictable and controlled responses as required by their application as implants with fixation to living tissue. The most promising material among these smart ceramics is transformation toughened nanocrystalline zirconia. Specifically, compared with conventional (micron-sized) ceramic formulations, nanophase ceramic compacts made separately from nanometer sized spherical particles of zirconia have a better prognosis for an enhanced adhesion of osteoblasts (bone-forming cells), and at the same time, an decreased adhesion of fibroblasts (cells that contribute to fibrous encapsulation and callus formation events that may lead to implant loosening and failure).

Memory Lymphocyte Immune Stimulation Assay (MEL-ISA) tests show that titanium, which is extensively used as implant material is prone for metalosis. Although titanium can be regarded as biocompatible it is not necessarily immunocompatible for each and every patient. Zirconia is in this respect in a decisive advantage over titanium. Zirconia functions bioelectrically as living bone itself, which is the main reason for the occurrence of calcium deposition on zirconia in the bone. Another essential advantage of zirconia over titanium is the very low plaque deposition as well as the aesthetic advantages.

However, in order to function properly, zirconia implants require an interface that is contiguous with the surrounding bone. Currently, such a predicted tissue response at the tissue-implant interface is difficult to obtain. Previous research demonstrated that osteogenic cells are sensitive to several surface properties of biomaterials. Properties that influence the behavior of cells, including matrix production and calcification, can be grouped into three interrelated categories: surface composition, surface energy and surface (micro)topography. In the present invention it is found that apatite coated zirconia appears to have properties that are favorable for interfacing with surrounding bone.

Application of bioactive apatite coated zirconia for use in implants comes forth out of our own findings because the knowledge about how calcium phosphate coatings support bone formation is at best rudimentary. We can only speculate about the mechanisms underlying this interfacial process. It has been suggested that due to dissolution of calcium from the surface and by taking calcium and phosphate from the surrounding body fluid, the interfacial calcium concentration is increased to such a level that the apatite formation is induced.

Figure 13:
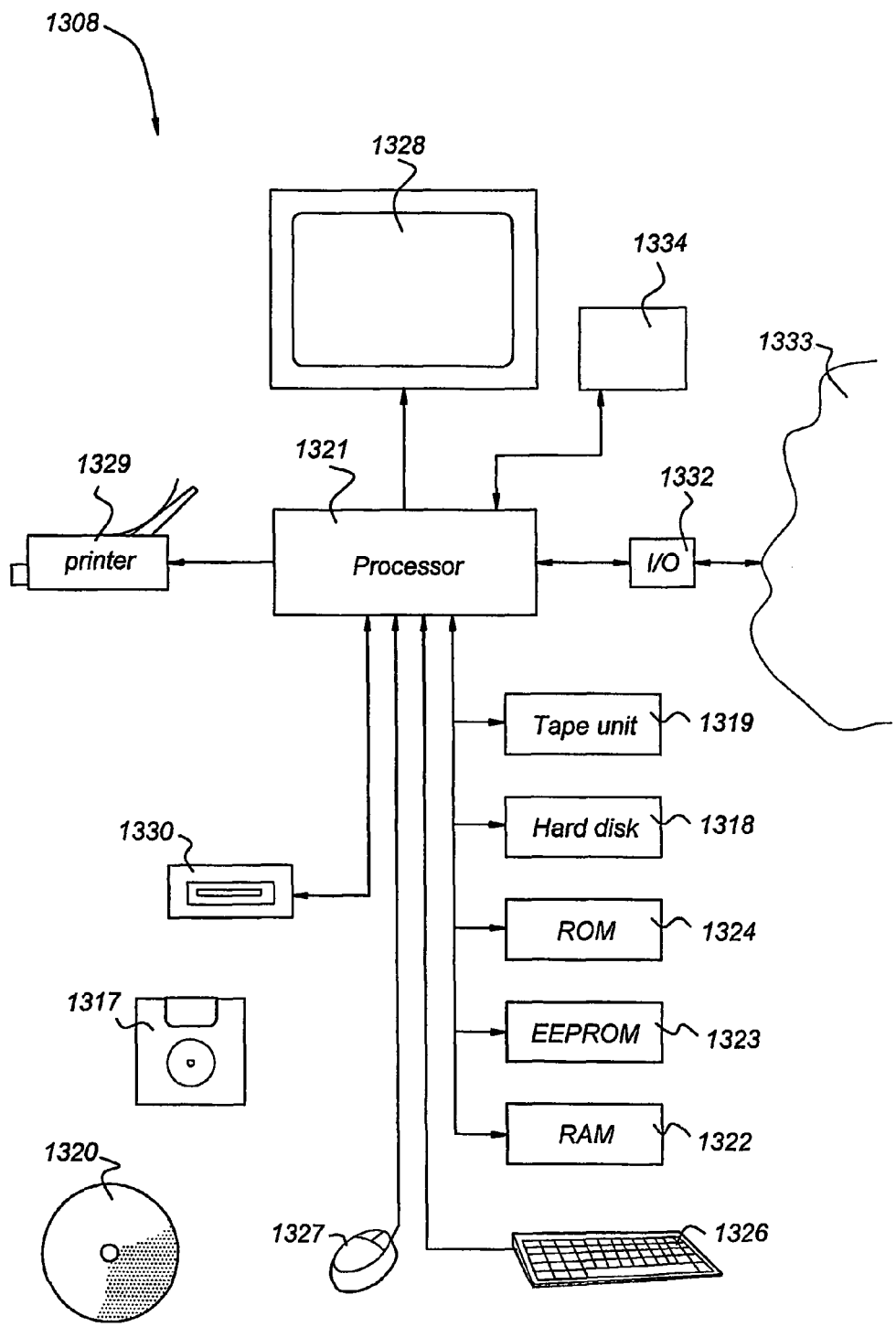
FIG. 13 shows schematically a computer system in accordance with the present invention.

FIG. 13 shows schematically a computer arrangement as used in the system according to the present invention. Computer system 1308 comprises host processor 1321 with peripherals. The host processor 1321 is connected to memory units 1318, 1319, 1322, 1323, 1324 which store instructions and data, one or more reading units 1330 (to read, e.g., floppy disks 1317, CD ROM's 1320, DVD's, a keyboard 1326 and a mouse 1327 as input devices, and as output devices, a monitor 1328 and a printer 1329. Other input devices, like a trackball or a touch screen as well as other output devices may be provided.

Further, a network I/O device 1332 is provided for a connection to a network 1333.

Finally, the host processor 1321 is connected to a scanning device 1334 capable of capturing 3D image data from objects. The 3D image data may comprise surface data of the object being scanned. The surface data may relate to any measurable property of the object such as color, 3D-geometry, transparency and opalescence (mamelons).

Also, the host processor is capable of importing data from another computer system by reading data from a data carrier or through the network connection.

The memory units shown comprise RAM 1322, (E)EPROM 1323, ROM 1324, tape unit 1319, and hard disk 1318. However, it should be understood that there may be provided more and/or other memory units known to persons skilled in the art. Moreover, one or more of them may be physically located remote from the processor 1321, if required.

The processor 1321 is shown as one box, however, it may comprise several processing units functioning in parallel or controlled by one main processor, that may be located remotely from one another, as is known to persons skilled in the art.

The computer system 1308 shown in FIG. 13 is arranged for performing computations in accordance with the method in accordance with the present invention.

FIG. 1 shows a schematic view of the special impression tray with reference spheres on a gypsum cast of a dentures impression.

In FIG. 1 is shown: an orientation device 11, an elastomeric impression of the preparations 12 and a gypsum duplicate cast of the preparations 13. The orientation device 11 is fixed to the silicone impression by retention pins or glue. It consists of a triangle, preferably made of a non-radio-opaque material such as plastic, with three sides with different lengths, with on each corner fixed a calibrated radio-opaque ball, preferably zirconia.

The metal free impression tray has fixed to it the triangle 11 comprising at each of its corners one calibrated ball 14 for merging with the bone structure.

During the first CT scan (Scan I) the impression tray with the balls is in place in the mouth of the patient. The patient is scanned in the CT device with the silicone impression 12 with the orientation device 11 placed in the mouth.

As shown in FIG. 1, the objective of the radiographic scanning is to obtain a three-dimensional computer graphics model of the patient's implant jaw which is provided by the computer system (1308). Images of the reference spheres 14 in the model provide a reference to a coordinate axes optical measuring machine and allow a merging with CT scan images of the jaw bone as will be discussed with reference to FIG. 5a.

The distances between the radio-opaque balls are known to the computer. Because the distances between each pair of them are different, after selecting the position of each of the balls 14 on the screen the orientation and position of the orientation device can unambiguously determined by the computer.

The radio-opaque balls show up in the CT X-ray scan in the same way as the zirconia implants are, however another radio-opaque material may also be used for the balls.

As illustrated here, the present invention provides a method for linking an orientation of a CT scan with an orientation of a denture impression.

In the present invention the orientation and place for a drilling hole in the drilling guide is determined from the CT scan imaging of the implant position and its orientation. Such a drilling hole allows the insertion of a tube that has a shape which is substantially the same as the shape of the drill in the hole that is incorporated in the model during the rapid prototyping of the drilling guide.

For designing the drilling guide the grey scale value data of the CT scan image information of the muscles and tendons which have to be taken into account when planning the implant position and orientation are in most cases insufficient to directly produce a drill guide's inner surface.

The inner surface of the drill guide in the present invention is not based on grey scale values of the CT scan image information of the muscles and tendons but on an accurate optical scan of a gypsum cast model of the gum and teeth obtained by an accurate impression.

The manipulation of digital image data during the preparation of a surgical implant drilling operation, for example, is known as such. It is possible, for example, to determine the position and direction of an implant on the images or to simulate surgeries. However, there is no connection with reality and, by lack of reference, these prepared image data cannot be used for the accurate design and production of the drilling guide. Therefore in the present invention the gypsum model is poured from an impression 12 made from the patient's mouth and scanned accurately with a laboratory optical scanning device. The images from the CT scanning and the laboratory optical scanning image are merged into a composite image using the three sphere reference device 11 fixed to the impression tray placed in position in the patient's mouth during CT scanning.

A merge operation is carried out by the computer system by performing a transformation (rotation and translation) of one scan image relative to one or more other scan images. Since the position and orientation of the orientation device 11 can be unambiguously determined by the computer system in each scan image, the required transformations in a merge operation can be calculated (and performed) from differences between the position and orientation of the respective scan images to be merged. Thus, the merge operation provides a coincidence of the scan images in such a way that a single composite image of both scan images is produced wherein position and orientation of both scan images are matched and substantially no mismatch between data from one scan image and the other occurs.

Note that since the respective scan images are taken by different methods, the data in the composite scan combines image data which can relate to the bone structure as well as to softer tissues like the gum.

Figure 2:
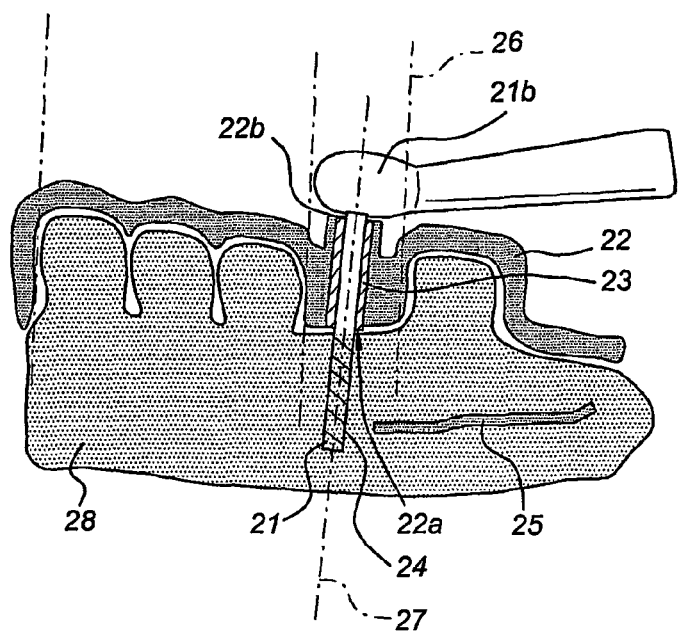
FIG. 2 shows a sectional view of the drill guide being used to drill a patient's jawbone.

FIG. 2 is a schematic cross-sectional view of a drilling guide for an implant with the aid of a drill in a hand piece.

On a model of a jawbone 28 and denture a drilling guide 22 is located. The model of the jawbone and denture may be a precise copy of a patient's jawbone and denture as obtained by a CT Scan and the optical scan, the images of both scans merged into a composite image of jawbone and denture. The objective of the drilling guide 22 is to assist in providing a location and orientation of the drill that upon use of the drill by the dental surgeon results in a substantially optimum location and orientation in the jawbone for the implant hole and for the implant placed inside the implant hole. The drilling guide 22 comprises a guiding hole 22a with a location and orientation relating to a desired location of the drill hole in the jawbone.

Thus, the software program which creates the drilling guide is arranged to accurately follow the surfaces of the images in order to obtain a shape for the drill guide 22 which, during use of the guide 22, allows a precise and stable positioning of it in the patient's mouth.

The drilling guide 22 typically consists of a methacrylate body with a guiding hole 22a. In the guiding hole 22a, a tube 23 is positioned, which diameter is adapted to the diameter of a drill 24 and the implant under construction. Preferably, the tube 23 consists of titanium or titanium alloy.

In FIG. 2 also a location of the nervus maxillaris 25 is shown.

For the drilling guide to go easy on the remaining teeth and the soft mucosa, it is imperative that there are no undercuts when placing the drill guide in the patient's mouth. Therefore, the software program for creating and manufacturing the drilling guide 22 will take care that any undercuts are removed in the direction of the path of insertion 26.

During treatment, the dentist drills the hole (in the jawbone) using drill axis 27 orientation through the titanium tube 23 until the hand piece 21b hits the drill guide 22 a drill stop 22b at a pre-calculated height, formed by a drill hole cylindrical build-up for stopping the drill in the jawbone at the depth equal to the difference of he length of the drill and the pre-calculated height of the tube 23.

The dentist is able to define through the implantation drill guide 22 with the axially correctly aligned drill tube 23 (as obtained from the CT scan), a perfect transfer of the prosthetically correct implant position.

As will be appreciated by persons skilled in the art, the oral surgeon is able to prepare the implant holes using the drill guide 22 by removing circular portions of the gum (gingival taps) at the location of the implant hole. In the conventional method of drilling implant holes, a procedure known as "flap surgery" is carried out in which a piece of the gum covering the jawbone where the implant hole is to be drilled is cut and peeled back so that the oral surgeon has clear access to the jawbone surface. Using the present invention, the surgeon has the option of doing either flap surgery if required or circumferential surgery as needed. If the circular approach is chosen, there is no need to remove the guide during surgery, and by avoiding flap surgery, post operation healing time should be reduced.

The position and the orientation of the implant, both in relation to the bone and in relation to the teeth is planned in a CT Scan Space Viewer. The CT Scan Space Viewer is implemented as computer program on a computer, which is capable of analyzing a computer generated representation of the image data, manipulating such a representation and compute from this representation data related to the drilling guide template 22. As mentioned above, first, a dental impression is made, a reference device applied and a tomographic (CT) scan with the impression in place in the mouth of the patient, is made. Thanks to computer-aided preparations of the CT scan Space Viewer, the thickness, position, direction and length of an implant can be well planned. These data related to the implant are subsequently used for the design of the drilling guide template 22. The CT Scan Space Viewer is capable of storing all planning related data in a computer memory for later use when making the drilling guide template 22.

By making a template according to the invention as represented in FIG. 2, it is not only possible to match the planned size and length of the implant in reality, but also directly its position and direction. The drilling guide is designed without disturbing undercuts which fit perfectly to the mucosal surface and remaining dentition and the tube element 23 which forms a guide for the drill bit 24 with which the hole for the implant is drilled and which determines the position, orientation and depth of the implant hole.

Figure 3A:
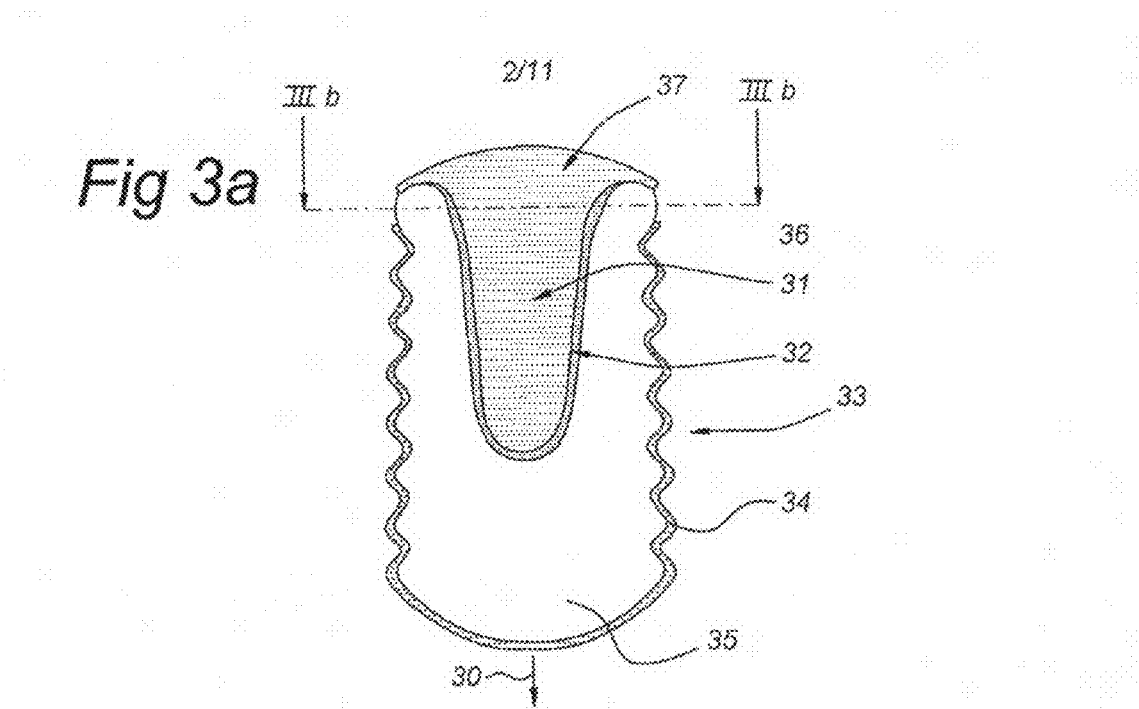
FIG. 3 shows a cross section of a ceramic implant according to the present invention.
Figure 3B:
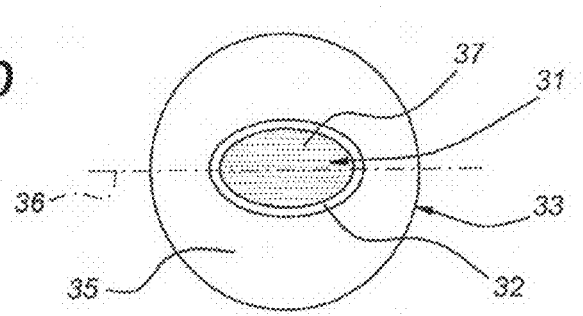

FIGS. 3a and 3b show a simplified diagram of an implant 33.

FIG. 3a shows a cross-sectional side view of the implant 33 perpendicular to the insertion direction 30. The implant 33 comprises a structural body 35, a recess 31 and a surface coating 34 according to an embodiment of the present invention. The recess 31 is arranged for receiving an abutment body. Here, the implant is shown with the recess 31 being covered by a healing stud 37, as used during the healing period after installing the implant in the jawbone.

According to the present invention, the structural body 35 consists of zirconia. The healing stud 37 may consists of propylene and may be held in the recess 31 by a temporary cement e.g., a zinc eugenol cement. The surface coating 34 comprises a mixture of zirconia and crystalline hydroxyapatite or fluorhydroxyapatite. The application of the coating will be discussed in more detail below.

Dashed line 36 indicates a center line across the implant 33 at a first height of the implant.

FIG. 3b shows a cross-sectional view of the implant parallel to the insertion direction 30 along the dashed line 36 of FIG. 3a.

In this cross-section the structural body 35 is shown in which the healing stud 37 is embedded. The healing stud is surrounded by the cement 32. from FIG. 3a and FIG. 3b it follows that the recess 31 in the structural body 35 holding cement 32 and healing stud 31, has (in cross-section) an ellipsoidal shape.

At a later stage, this shape can be used for detection of the maximum diameter orientation (along dashed line 36) by a second CT scanning at the second CT scan after osseointegration of the implants has taken place.

The implant connection by the recess 31 in the structural body 35 with an aesthetic abutment or abutment crown is very important and must give the restoration in function a stable anchoring.

Figure 4A:
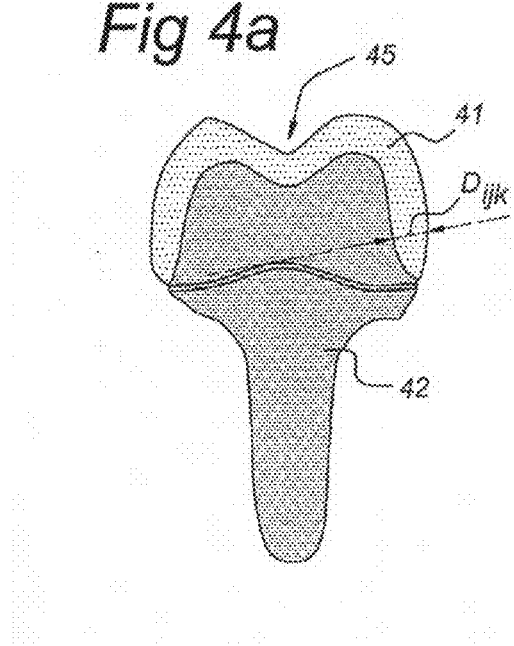
FIG. 4 shows a cross section of the aesthetic implant abutment or abutment crown in accordance with the present invention.
Figure 4B:
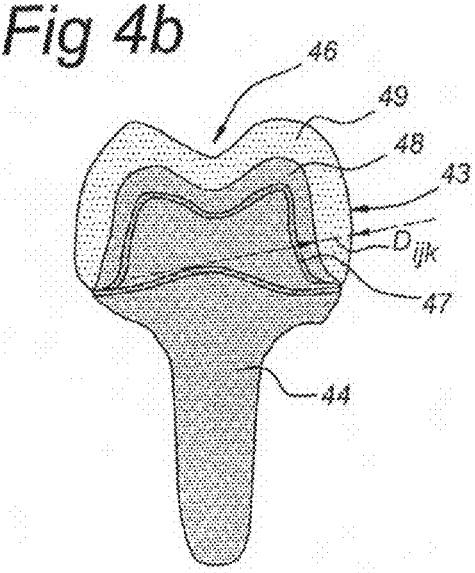

FIG. 4a and FIG. 4b show schematically a cross-section of aesthetic abutment 45 or abutment crown 46, respectively, according to an embodiment of the present invention.

The abutment 45 comprises an abutment body 42 and a cap 41. The cap 41 covers the top of the abutment body 42.

The abutment crown 46 comprises an adapted abutment body 44 and a composite cap 43. The composite cap 43 consists of support structure (a coping) 48 and a second cap 49 which covers the top of the support structure 48. Composite cap 43 is connected to adapted abutment body 42 by a connecting layer 47, possibly a cement or glue compound.

The mail extension shape of abutment body 42 and adapted abutment body 44 is complementary to the female recess shape of the recess 31 in the structural body 35 of the implant.

The possibility of a direct fit of the male extension of abutment body 42; 44 into the conical ellipsoidal female recess 31 in the implant is an advantage over existing implant systems that have more interfaces (for example, with a square or hexagonal cross-section) and as known to persons skilled in the art, every interface can cause possible instability.

The abutment body 42; 44 is self cantering at placement which is almost "self finding" because of the conical shape of the extension and recess 31. The absolute rotational security because of the elliptically shaped connector (see FIG. 3b) is one of the most important biomechanical parameters for a secure therapy.

According to the present invention, the abutment body consists of zirconia. The cap 41 or second cap 49 consists of a translucent veneering material.

The thickness ($D_{i,j,k}$) of the cap 41; 49 is varied by the external dimensions of the colored opaque abutment body 42. The abutment body forms the background in order to arrive at the right color at the external surface of the cap of the abutment or abutment crown.

The task of replacing a tooth with a prosthesis which by its shape and colour does not substantially differ from the other teeth, is conventionally made of two separate steps. The first step is to measure the shape and color shade of a tooth to be replaced and the second step is to make a duplicate of that tooth according to the measurements taken in the first step.

To obtain color information of a tooth a line scanning data acquisition method is used, in which a controlled white light illuminates the visible part of the tooth. The reflected light is recorded by means capable of detecting spectral information from the reflected light. In the art, such spectral information is typically defined in accordance with a standard known as the CIE lab color standard.

It is to be noted that the line scanning data acquisition method may provide a high spatial resolution in the direction perpendicular to the scan direction. However, there is a trade-off between the spatial resolution in the scan direction and temporal resolution. Since the dental industry does not use the CIE LAB color to communicate tooth color, but a color shade guide provided by the manufacturers of the ceramic powders used to manufacture dental prosthesis, the CIE lab color results must be further processed. Different digital measurement techniques are presently used to quantize the reflected light coming from an illuminated object. These techniques usually consist in a spectral decomposition of the reflected light from a selected area of the object surface. To get a natural appearance of the abutment or abutment crown one or more layers of translucent tooth colored glass ceramic (i.e., the cap 41; 49) are necessary on the abutment body 42; 44. The abutment body is pigmented, to obtain a tooth color (In CIE-lab numbers: $L^*=79.6$, $a^*=5.4$, $b^*=25.1$).

The method used comprises five steps:

1) establishing the available outer shape and dimensions of the abutment or abutment crown in contact with the opposing teeth and the adjacent teeth using design software;

2) acquiring an image of a natural tooth to be replaced by the artificial tooth or corresponding natural tooth over at least the in use visible outer surface thereof, including variations in appearance in said outer surface;

3) determining variations in the appearance determining properties of the cover layer i.e., cap 41; 43 to correspond with the variations in the appearance of the corresponding natural tooth, and determining the thickness of the cover layer ($D_{i,j,k}$) locally (in a (three-dimensional) i, j, k—coordinate-system) required for said correspondence (see FIG. 12);

4) constructing the top part topography of the abutment body 42; 44 to a shape and dimensions, which are based on the shape and dimensions available for the artificial tooth, and prior to construction deducting in the design software from the shape and dimensions, the locally required thickness $D_{i,j,k}$ of the cover layer (cap 41; 49); and 5) applying the cover layer (cap 41; 49) over the abutment body 42; 44 to obtain the available outer shape and dimensions for the finished aesthetic abutment or abutment crown.

In FIG. 4b a smaller adapted abutment body (44) with the support structure or coping 48 is shown with the second cap 49 which is substantially the same as cap 41. Here, the abutment can be cemented first and a separate crown consisting of the support structure or coping 48 and a glass ceramic cover layer, cap 41; 49 can be cemented on the adapted abutment body 44.

FIG. 5a is a schematic view of an implant with the prosthetic device in place according to the present invention.

The abutment or abutment crown 45; 46 is in occlusal contact with an antagonist tooth 51 with the occlusal surface of the cap 41; 49 of the abutment making contact with antagonist tooth 51. Antagonist tooth 51 is connected to opposing jaw bone 57b.

The implant is implanted in the jawbone 57. The jawbone 57 is surrounded by mucosa 58.

The abutment 45; 46 is cemented in the recess of the implant 35 with a cement 32, for example Panavia F (Kuraray of Japan), a composite cement with phosphate groups.

Marginal line 54 on the abutment 45; 46 defines a delineation with the mucosa, as it will occur after a healing period. This will be explained in more detail below.

According to a preferred embodiment of the present invention the design of the abutment 45; 46 is such that a plane-to-plane contact between the abutment crown and the implant is absent.

Advantageously, the conical recess receives the implant extension which extends in the same conical direction with a open circumference 59, leaving the possibility for future mucosa to grow into the space between the abutment crown underside and the top of the implant along the open circumference 59. A plane-to-plane contact can at the outside of the line of contact cause a ridge, which can be the cause for plaque formation.

In case of this shape of the abutment there will be no such ridge because the conical parts meet on the outside into a sharp ending recess line and not a plane-to-plane contact line.

A good design between localization of the mesial and distal contact against adjacent teeth makes fitting the prosthetic device possible in a stable fitting position in the row of teeth in the jaw. In the prior art, with respect to a fit between adjacent teeth, a dentist will grind and polish the prosthetic device to obtain the final fit of the prosthetic device in contact with its neighboring and opposing teeth.

Figure 5B:
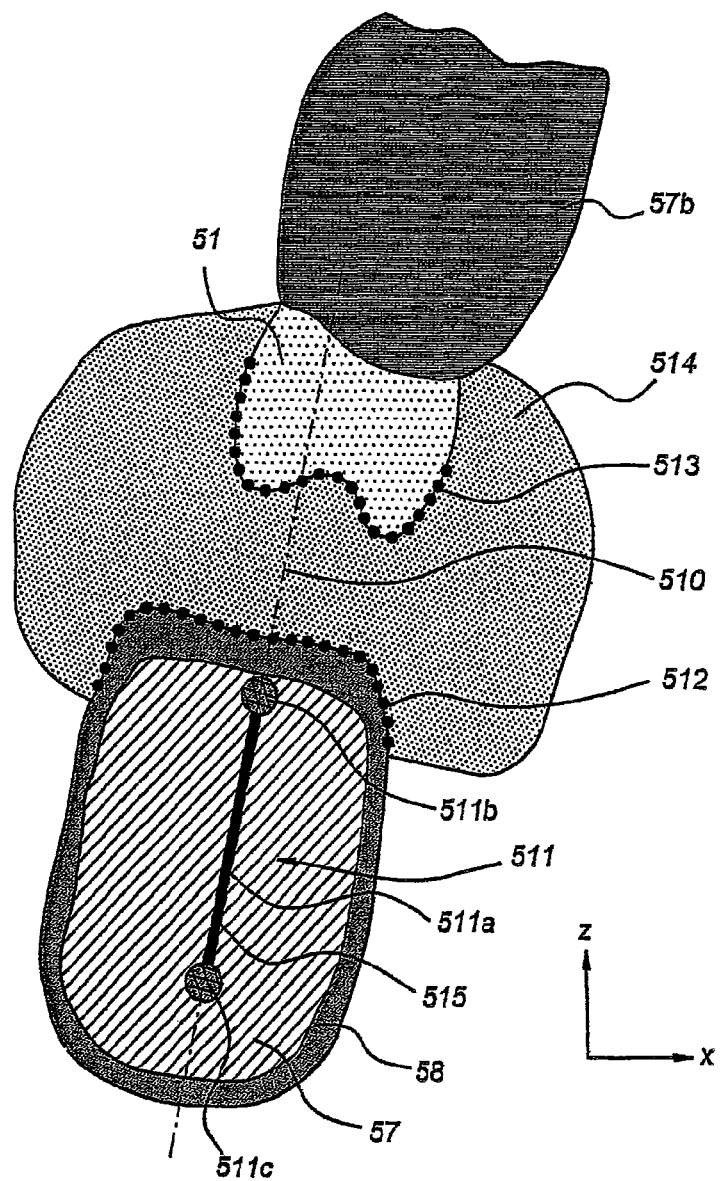
FIG. 5b shows a sectional view indicating the drill axis with the bottom location and the mucosa or top location of the implant in relation to the opposing teeth surface, the implant jaw surface, and a location of the registration bite impression.

FIG. 5b is a schematic view of a registration bite impression material 514 of the antagonistic teeth 51.

In accordance with the present invention this registration bite is taken on the open location of the implant to be constructed.

Later, when the scan of the registration bite ("Registration Scan") is merged with the CT scan of the bone structure ("CT Scan I") the operator can clearly evaluate how the direction and position of the implant, the bottom location and the location of the mucosa 58 ("Jaw Scan") of the implant and the aesthetic abutment or abutment crown is going to interact with the antagonistic tooth 51 in terms of loading. When the loading is more or less in line with the (designed) drill axis of the implant 510, the implant will encounter relatively small lateral loading, which results in a more durable implant functioning. As can be appreciated, two angles are required to specify the orientation of the drill axis 27, for example, a first angle may define an angle of the drill axis 27 with respect to a x-z reference plane and a second angular parameter may define the angle between the drill axis 27 in the z-y reference plane (which is preferably orthogonal to the x-z plane). In FIG. 5b the plane of the drawing is taken as the x-z reference plane.

As illustrated in FIG. 5b, in the preferred embodiment, it is possible to view for the selected drill axis 510 a resulting implant position and orientation 511 (defined here by its main axis (and its orientation) 511a, its upper and lower endpoints 511b and 511c) and how this position relates to the bone structure 57, the nerve 25, if present, as well as the opposite teeth 51. Note that the image as schematically depicted in FIG. 5a, contains the above-mentioned information from the first CT scan, from the optical scan from the gypsum cast and from the registration bite.

The dental surgeon is able in the computer model to select the optimum depth, position and angular orientation for the implant 511 (511a, 511b, 511c) relying entirely on the computer model. Once the hole termination position and angular orientation data for (each of) the drill hole(s) is selected using the computer model, the data for the design are sent, together with the reconstructed surface data of the implant jaw, to a centralized stereolithographic facility. There, the data for the design are used to manufacture the drilling guide 22 as described above.

Figure 6A:
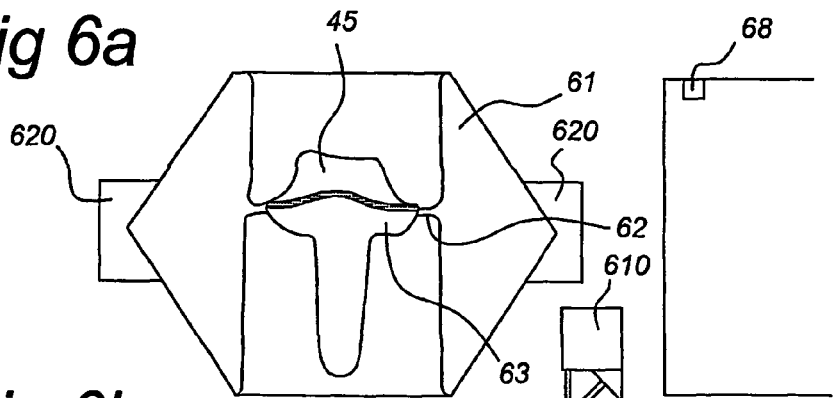
FIG. 6 shows a flow diagram of the manufacturing steps for the aesthetic implant abutment or abutment crown.

FIGS. 6a, 6b, 6c, 6d and 6e give the production sequence of the aesthetic abutment 45:

FIG. 6a: A hexagon block 61 of isostatically pressed or injection molded yttria stabilized tetragonal zirconia polycrystalline (Y-TZP) zirconia was clamped on its two lateral sides in the prismatic clamping device 620 in a milling machine.

The underside 63 of the abutment 45 to be formed is milled leaving it about 0.1 mm short of the marginal line 54 of the mucosa 58.

Next, the hexblock 61 is given a calibrated reference hole 68 which can be sensed in the clamping device and can be used for repositioning in the longitudinal direction after sintering.

Then, the hexblock 61 is turned and the top side of the abutment 45 is milled up to the marginal line 54, leaving a retention ridge all around 62.

The block is sintered at high temperature e.g., 1550° C. during a suitable time, and experiences a shrinkage of about 19-25%.

Figure 6B:
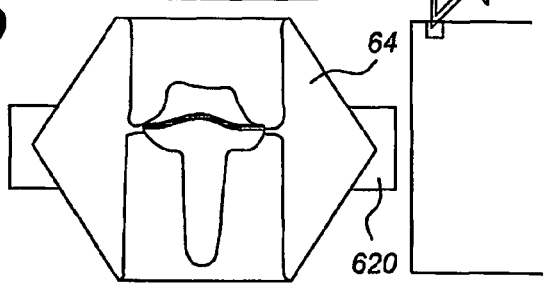

FIG. 6b: The sintered hex block 64 block is repositioned in the prismatic clamping device 620. The longitudinally position is measured up by way of optical detection 610 of the calibrated reference hole 68 that was milled in the previous step in the unsintered hexblock (FIG. 6a).

Figure 6C:
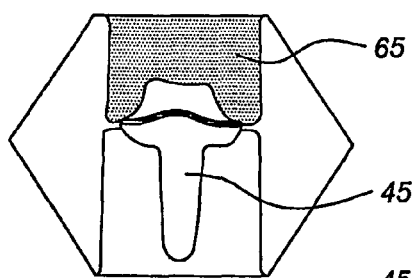

FIG. 6c: Veneering material 65 is pressed over the top side of the abutment 45 in the form of a paste of a glass ceramic having the same or a slightly lower linear thermal expansion coefficient as the zirconia-based abutment core. The veneering material is then hardened or sintered during a suitable heat treatment to form the cap 41 of the abutment 45.

Figure 6D:
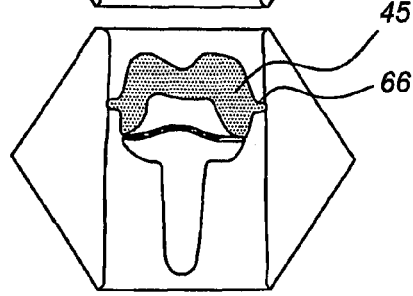

FIG. 6d: The veneering material is milled from the top but left short about 0.1 mm from the equator 66 of the cap 41, leaving a rim on the equator 66. The retention ridge 62 is removed during the milling of the cap 41.

Figure 6E:
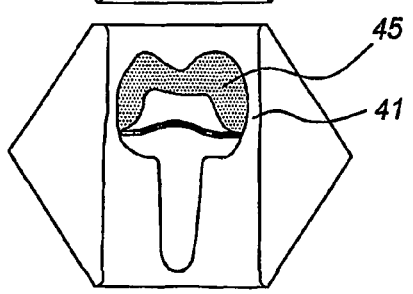

FIG. 6e: The rim on the equator 66 is finally milled away and the aesthetic abutment or abutment crown is finished. The aesthetic abutment 45 is given a final polishing, and the veneered part 41 is individualized by staining.

Note that the milling process can be used also for fabrication of the adapted abutment body 44 for an abutment crown 46, up to the step shown in FIG. 6b.

The composite cap 43 comprising a support structure 48 and a cap layer 49 may also be made by a milling and sintering sequence, which starts out with the modeling of the support structure, followed by the manufacturing of the cap layer 49.

Figure 7:
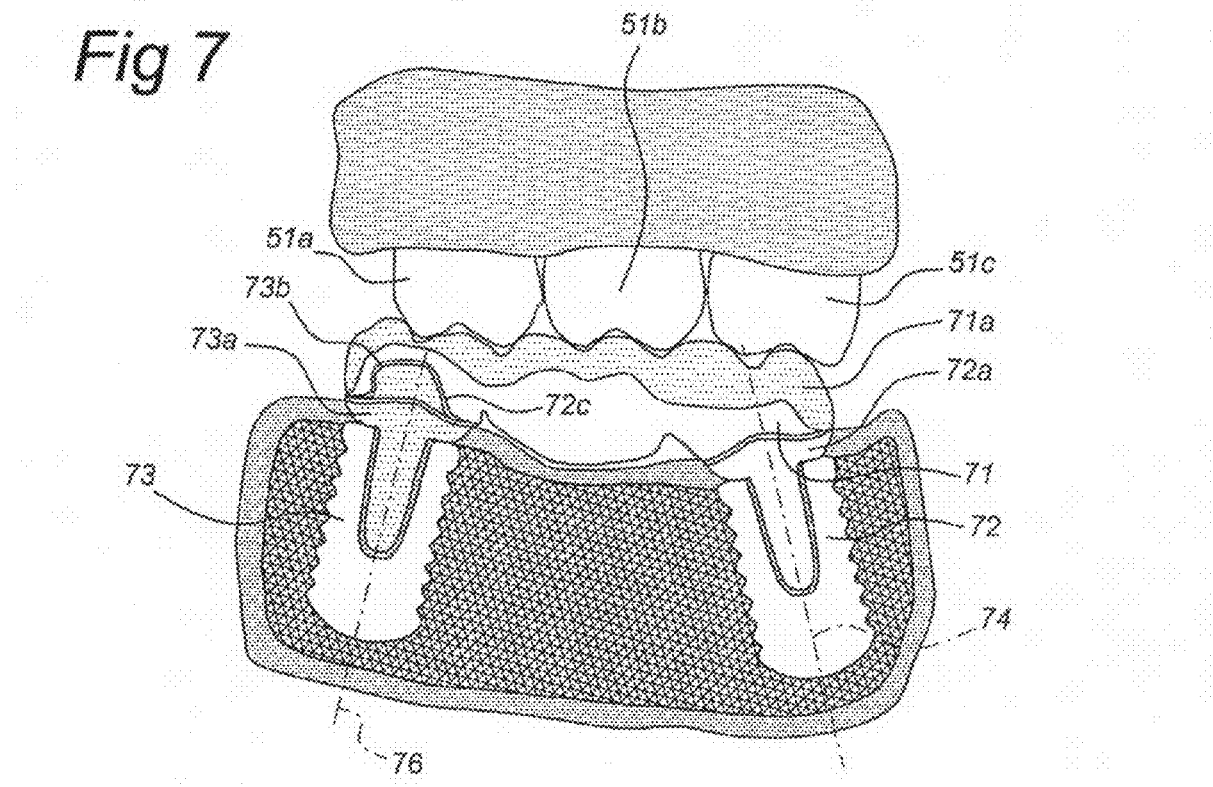
FIG. 7 shows a sectional view of a bridge comprising two diverging implants in accordance with the present invention.

FIG. 7 is a schematic example of a bridge construction 71 on two deviating (non-parallel) implants 72, 73.

The bridge construction comprises two implants 72 and 73, each equipped with an abutment 72a, 73a, and a cap layer 71a. The implant 72 has a main insertion axis 74, and the implant 73 has a second insertion axis 76.

The abutment 72a extends under a plurality of antagonistic teeth (shown here as three teeth 51a, 51b, 51c). The cap layer 71a forms a veneering layer over the full top side of the abutment 72a, i.e., cap layer 71a and abutment 72a are designed to replace the (three) teeth below the antagonistic teeth 51a, 51b, 5c.

To create a same path of insertion 74, the direction of the abutment 73a of one of the implants (73) is made to coincide in direction with the implant 72.

The abutment 73a is not directly connected to the cap layer 71a of veneering material, but is allowed to be disconnected.

In case of more than two deviating implants, the implants also are disconnected with the veneering material and the bridge construction is fabricated separately from the abutment to allow for proper insertion.

Note that the shape of cap layer 71a and of the abutment 72a can be designed and manufactured in a similar manner as an abutment 45 for a single tooth replacement.

The other abutment 73a is similar to an adapted abutment 44 as shown in FIG. 4. Note that an interface 73b between abutment 73a and a portion 72c of abutment 72a exists. The portion 72c and the top side of abutment 73a can be shaped during the design and manufacturing process in such a way that a sufficient mechanically stable match at the interface 73b is present. The interface 73b may provide a space for a cement for joining abutment 73a and abutment 72a.

Figure 8:
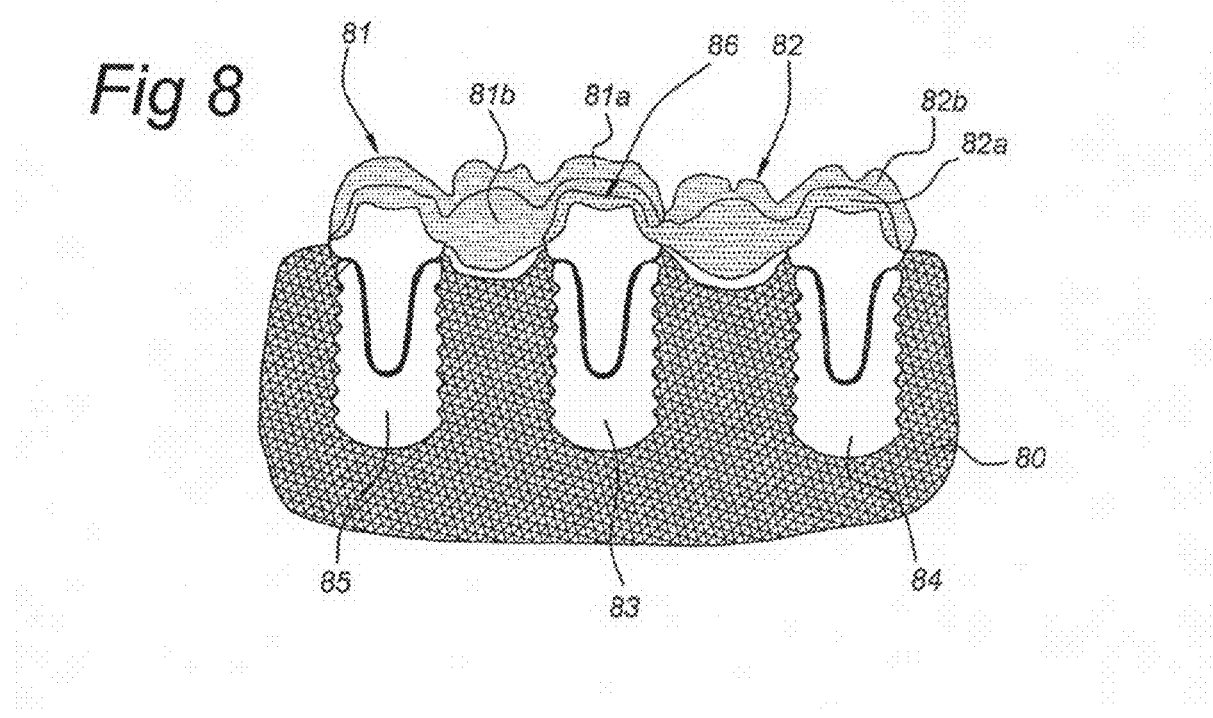
FIG. 8 shows a sectional view of two separate bridges in accordance with the present invention.

FIG. 8 is a sectional view of an extensive restoration consisting of two consecutive bridges in a jawbone 80. A distal bridge part 82 is forming a first capping of a middle implant element 83, while an anterior bridge part 81 is overcapping the first capping of the distal bridge part 82.

The distal bridge part 82 is a bridge construction between the middle implant element 83 and a further implant element 84. The distal bridge part 82 comprises a distal abutment part 82a extending between implant elements 83 and 84 and a distal capping layer 82b.

The anterior bridge part 81 is connected to still a further implant element 85 in the jawbone. The anterior bridge part 81 comprises an anterior abutment part 81a extending between implant elements 83 and 85, and an anterior capping layer 81b.

On top of middle implant element 83 an overlapping region 86 of the bridge parts 81 and 82 exits. Distal capping layer 82b of the distal bridge 82 covers the distal abutment 82a for most part except the overlapping region 86. on the overlapping region 86 the anterior abutment 81a covers the distal abutment 82a. anterior abutment 81 is completely covered on its top side by anterior capping layer 81a.

This way large bridge constructions can be made in different parts, allowing for some minor movements and slight imprecisions of the implant positions or the bridge parts. Basically, the bridge construction follows the method as disclosed with reference to FIG. 7: the design and manufacture of each abutment and cap layer for the respective bridge part 81; 82 is such that still a sufficiently stable match between them can be made.

Figure 9:
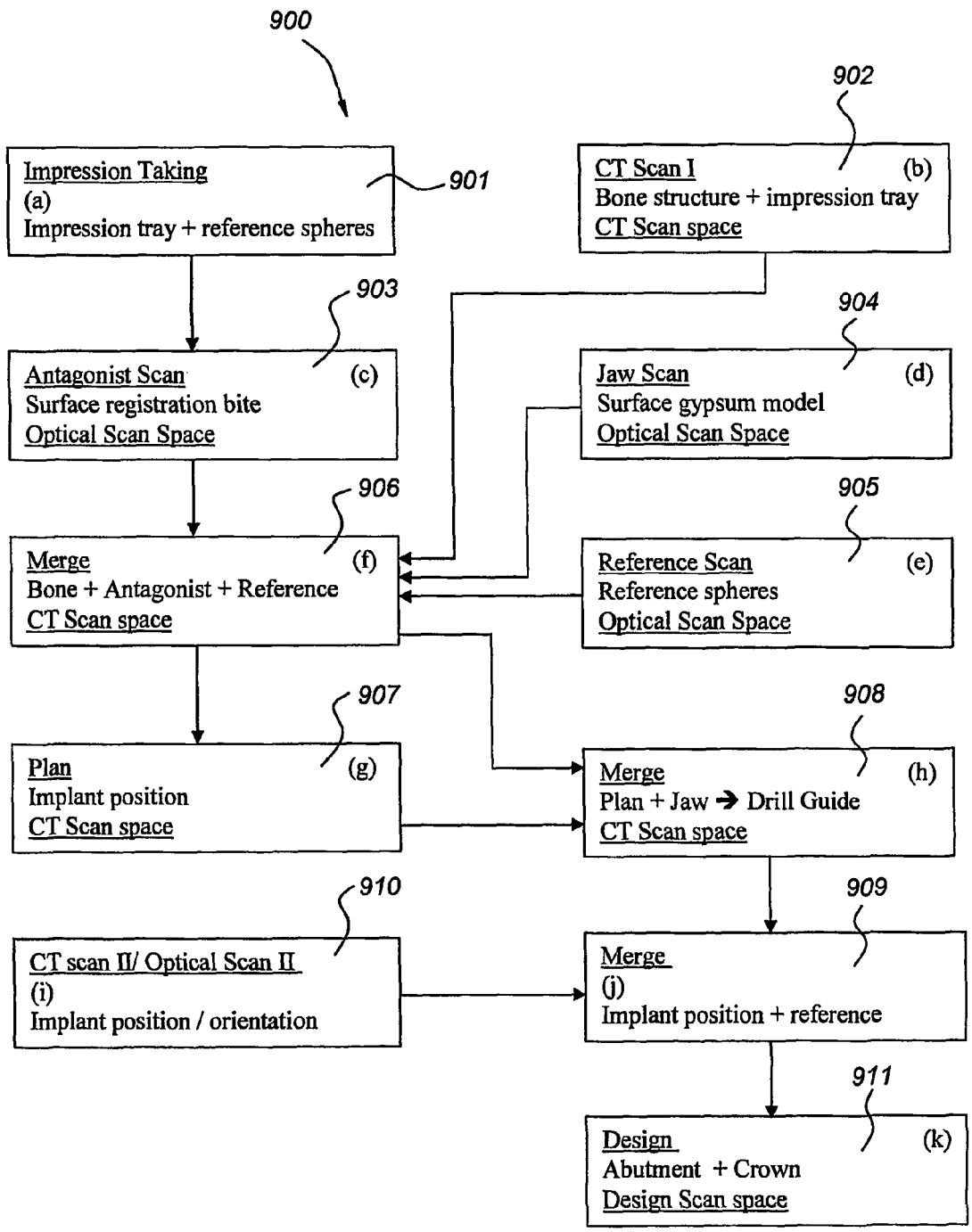
FIG. 9 shows a flow of the scanning sequence using a combination of CT and optical scanning and merging algorithms for the planning and placement of implants and the design and the manufacturing of an aesthetic implant abutment.

FIG. 9 shows a flow diagram for a scan sequence 900 in accordance with the method of the present invention.

In a first step 901, the patient is first diagnosed for a treatment with implants. After patient consent at the first visit, the dentist takes an impression of the dentures with the special non-metal tray 12 with, for example, three or more calibration spheres 14 at fixed and known distances fixed on the impression tray. The calibration spheres 14 consist preferably of zirconia and have for example a diameter of 4 mm Next, the impression is cast in gypsum (gypsum model 13).

Then, the dentist takes with another impression material or special bite wax an impression 514 of the antagonists 51, whereby the patient strongly bites the teeth in a deep, central static occlusion. After complete hardening of the impression material the dentist removes the impression from the mouth of the patient (registration bite).

In step 902, the patient is scanned by CT scanning with the impression tray with three calibration balls in position in the mouth of the patient (CT Scan I). During the CT scanning the bone structure is registered together with the three reference spheres 14 in the same coordinate system of the CT Scan Space of CT Scan I. The reference spheres are identified in one top and two side views of the CT Scan.

In step 903, the gypsum cast of the jaw impression is placed in the optical scanner in such a way that the path of insertion 26 of the drill guide coincides with the z-axis of the scanner.

The antagonist impression (registration bite) is placed with some seating pressure on the gypsum model, still in the same position in the scanner, and the registration bite impression surface is scanned optically (Antagonist Scan). The scanner provides an image of the gypsum cast. From this image the scan data (Optical Scan) are defined in a coordinate system of an Optical Scan Space.

In step 904, the surface of the gypsum model is now scanned (Jaw Scan). This surface is the basis for the definition of the supporting surface of the drill guide.

The antagonist impression (registration bite) is removed from the model. The impression tray with three reference spheres, is then placed on the gypsum model, which remained in the same positions as during the Antagonist Scan in the optical scanner.

In step 905, the reference spheres 14 of the impression tray are scanned (Reference Scan), so that their orientation in relation to the gypsum cast and thus the implant jaw and the antagonist orientation in the Optical Scan Space are known.

In step 906, the positions of the three reference spheres from the reference scan are merged with the antagonist surface data in the Optical Scan Space. These Antagonist Scan data and the Reference Scan Data are merged with the Jaw Scan bone structure data by means of mathematical transformation resulting from merging the reference spheres in the Optical Scan Space to the CT Scan Space. The necessary rotation and translation movements to match the position of the three reference spheres in the Optical Scan Space to their corresponding positions in the CT Scan Space is calculated. These calculated movements are used to match the implant jaw and the antagonist surface with the bone structure in the CT Scan Space for visualization by the operator.

In step 907, the dentist can now see the combined picture of implant jaw surface 512 and the antagonist surface 513 and the quality and quantity of the availability of the jawbone 57 in the CT Scan Space on his computer screen. The dentist is now able to (virtually) select the proper implant and place it in an appropriate position and orientation 511a, 511c in the jawbone, taking account of the position of the antagonists 51 with regard to aligning of the implant to cause minimal lateral loading of the implant, bone quality and quantity and surrounding risk structures (such as the nervus maxillaris 25), nose vacuole, etc. If more implants are to be placed, the orientation of the implants can be aligned by a parallelization software operation.

In step 908, the positioning data of the implants in the CT Scan Space are merged with the jaw surface data after modification for undercuts for the design of a drill guide 22. The inside surface of the drill guide is calculated using the Jaw Scan data and removing all undercuts in the direction of the path of insertion 26 which was visually determined during the positioning of the gypsum model in the clamping device in the direction of the vertical axis of the optical scanner.

Then, these merged data are converted from the CT Scan Space to the Design Scan Space coordinates. The drill is approximately 3 mm thick and at the location of the drill hole the drilling guide 22 has a cylindrical part that takes account of the drill length and the orientation and depth of the implant. The completed drill guide design data are send to a centralized production facility and produced by, for example, stereo lithography (SLA). In the drill guiding holes inserts are placed of titanium with an internal diameter adjusted to the diameter of the drill, which fits the chosen implant diameter and length.

The dentist uses the drill guide to punch a small perforation in the mucosa with an open drill. Then the proper drill is used to drill the implant holes taps. the screw thread and the implants are screwed into the prepared holes using the elliptical hole as a grip for a torque fastening tool with a corresponding shape. The dentists presses the healing caps 31 on the implants and closes the holes by stitching with suture wire.

In step 910, after a healing period a second CT scan (CT Scan II) is made of the patient's mouth with the impression tray with the reference spheres in position in the mouth of the patient. (The dentist checks the osseointegration status of the implant.) Alternatively markers are placed on the implants and an impression is made incorporating the markers. A gypsum cast is poured with implant dummies placed on the markers. The gypsum cast is scanned by the optical scanner (Optical Scan II).

The impression tray with the reference spheres is placed on top of the gypsum model in the optical scanner.

The position of the reference spheres in CT Scan II and Optical Scan II are once determined for merging with the implant jaw and antagonistic scans in the Design Scan Space in step 909 (as described above).

Also, the orientation and position of the implant(s) 35 as well as the orientation of the inner elliptical recess are merged with the Jaw Scan surface and the Antagonist Scan surface in the Design Scan Space. The CT scan II is capable to detect the longitudinal orientation 36 of the recess.

Now in step 911, the abutment 45; 46 can be designed in the surrounding of the mouth and in contact with antagonists and any possible neighbor elements. The orientation of the standard conically shaped retention part of the abutment 45; 46 is fixed, allowing for a 10-50 micron cement space 32. The outer shape of the aesthetic abutment or abutment crown 41; 43 can be adapted to the mucosa line 54 and designed into the space given by neigbor elements and the antagonists 51, of which the surface was registered with the registration bite in the previous visit. The thickness $D_{ijk}$ of the porcelain layer 41; 49 depends on the color measurements made on the corresponding tooth (as will explained with reference to FIG. 11).

For placing the abutment 45; 46, the dentist opens the place of the implant using a hollow drill and the drill guide to remove a round part of the mucosa, removes the (ethylene) healing cap 31 by use of a needle with a reversed hook and cements the aesthetic abutment 45 or abutment crown 46 in the recess of the implant.

FIGS. 10a-10e show schematically the production sequence of an implant as a part of the embodiment of the invention.

Figure 10A:
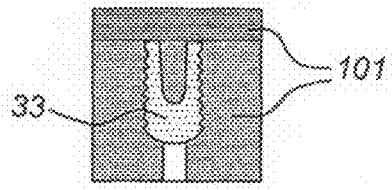
FIGS. 10*a*-10*e* show a flow of the manufacturing process steps for the ceramic implant with bioactive coating.

FIG. 10a: The implant 33 is injection molded in zirconia in a special casting form 101. The form 101 is oversized in relation to the final size, taking account of the sinter shrinkage.

Figure 10B:
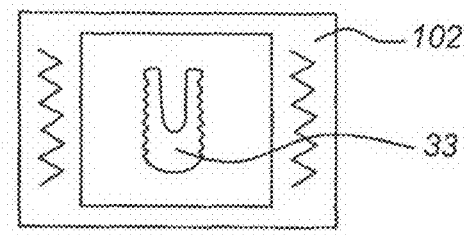

FIG. 10b: The injection moulded implant 33 is taken from a pre-heated split injection mold form 101 and placed in a furnace 102 at elevated temperature. Wax binder within the injection moulded shape is removed by heating slowly to a temperature of 450° C. for 3 hours in air.

Figure 10C:
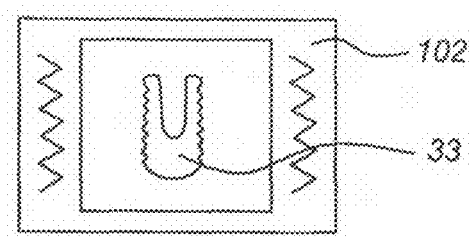

FIG. 10c: The implant is pre-sintered at 800° C. for 1 hour in air until neck forming has taken place to obtain a porous structure that is stable enough to be handled.

Figure 10D:
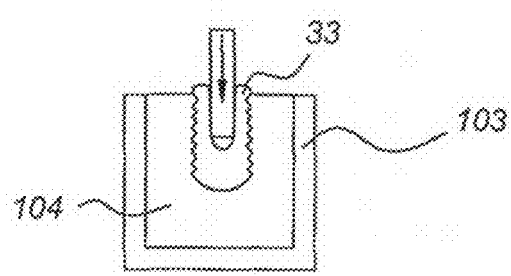

FIG. 10d: The pre-sintered implant is fixed in a precisely vertical position in a dipping machine 103 and submerged in a slurry 104 consisting of a mixture of apatite crystals (for example hydroxy-apatite) and zirconia in a carrier liquid, containing dispersing agents and binders. The implant is dipped and the slurry is deposited against the surface by membrane absorption of the liquid carrier.

Figure 10E:
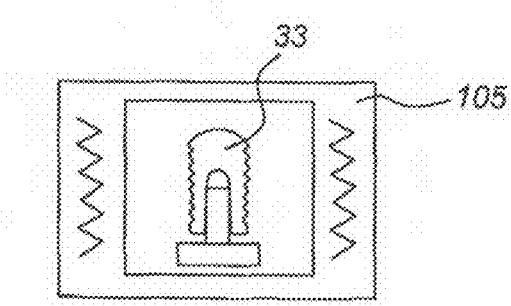

FIG. 10e: Next, the implant covered by a thin layer of the slurry is sintered in steam saturated air in a furnace 105.

The manufacturing is further discussed with reference to example I as given below.

Figure 11A:
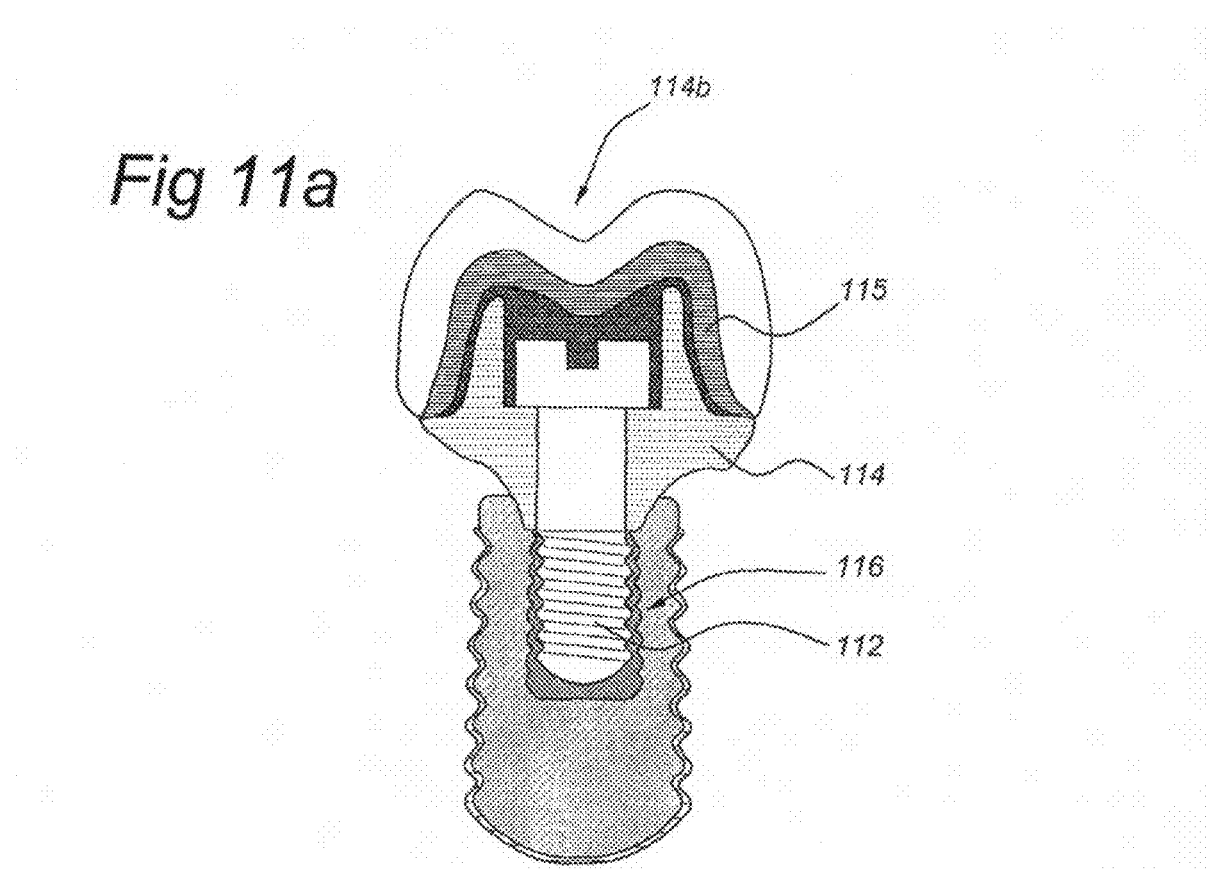
FIG. 11 shows two sections of alternative embodiments of the present invention with a screw connection of the abutment with coping and of the abutment crown.
Figure 11B:
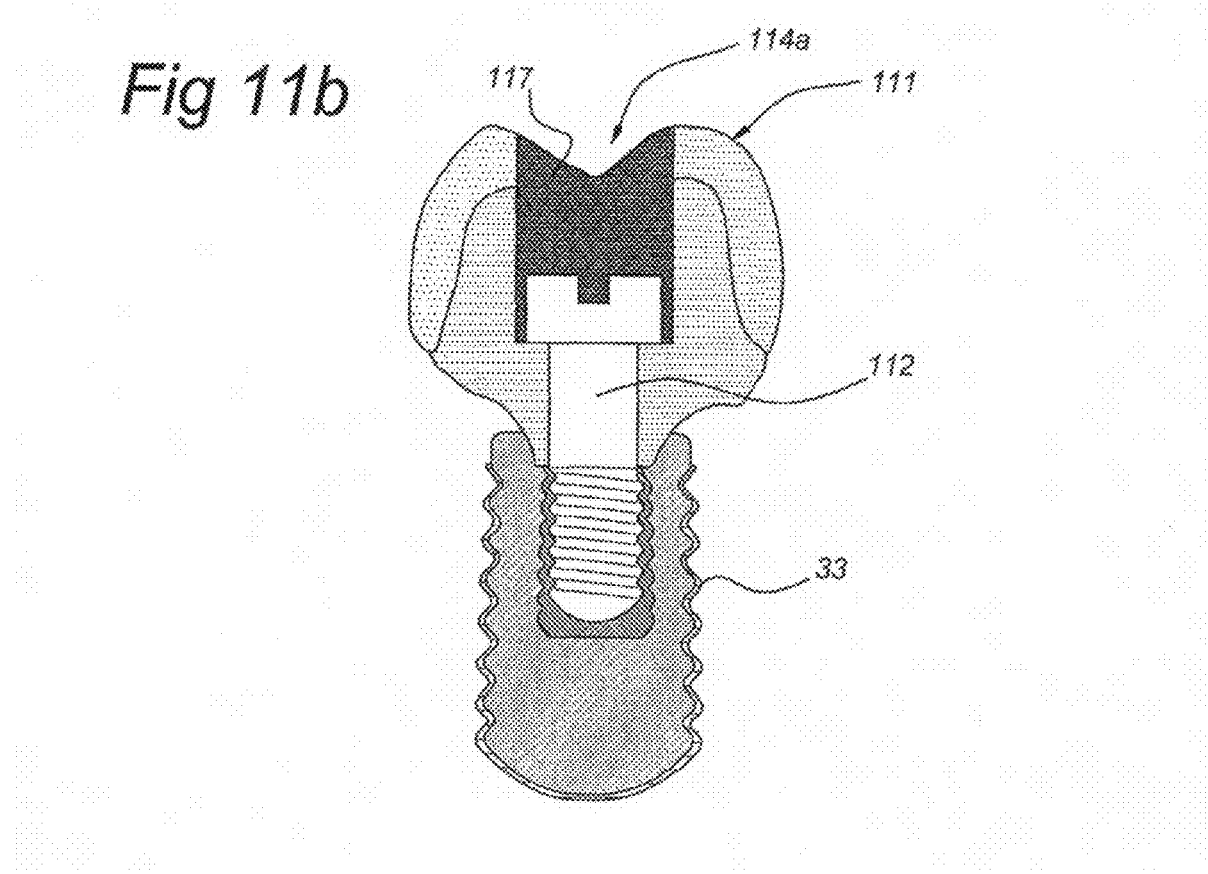

FIG. 11 show alternative embodiments of the invention in which retention with the implant 33 is not realized through cementation but through a screw 112.

The screw 112 is used for retention of an abutment (114a) or an abutment crown (114b).

Because of the absence of a central extension 42; 44 as shown in FIG. 4, a geometric extension 116 (for example cylindrical, hexagonal or octagonal) is necessary to center the abutment or abutment crown on the implant 33.

Similarly, as shown in FIG. 4 both a zirconia abutment 114 covered with a zirconia coping 111 or a zirconia abutment crown 115 are possible.

In the geometric extension 116, an internal thread can be provided by an metallic insert that is cemented in production or cut directly in the zirconia mass before final sintering.

In use, the abutment or abutment crown is screwed on the implant (after healing). Next, the hole in the abutment (crown) over the screw 112 is filled with a suitable filler material 117. In case of the abutment 114a, the filler material is shaped to complete the surface of the abutment as designed. In case of the abutment crown 114b, the coping 115 is placed over the filler material 117.

FIG. 12 shows a flow diagram for a computer calculated core coordinates determination of a color of the replacement tooth. First the color of a tooth T0 to be replaced is measured digitally in three regions at different heights: region A is located just below the mamelons, region B is located around the equator and region C is located at the cervical part of the tooth T0. It is noted that the number of regions and their locations may be chosen differently. In the simplest case only one region is measured, for example only just below the mamelons (which may be the region most visible).

The color expression model used for determining a color for a replacement tooth is based on supposition that the color as appearing to a viewer is obtained from a combination of a glass ceramic color and an abutment core color, with the abutment core color being transmitted through the glass ceramic. The color expression is governed by the thickness $D_{ijk}$ of the glass ceramic. Above a certain opacity thickness $D_0$ of the glass ceramic the transmission from the core is assumed to be substantially zero.

In a first approximation the combination is assumed as a linear relationship with the thickness $D_{ijk}$ of the glass ceramic layer.

The measurements from the three regions A, B, C are averaged to obtain a global indication of the "overall color" of the tooth. (The average may be either an arithmetic average or a weighted average with a weight factor for each region.)

The closest glass ceramic shade and the closest core shade of a selected prothesis are selected.

Then the method determines from the colors of the three regions A, B, C and the closest glass ceramic color and abutment core shade which value of the local distance or thickness $D_{ijk}$ of the glass ceramic layer results in the best approximation of the color of the original tooth T0. From these we calculate the local core coordinates.

Procedure 1200 of FIG. 12 illustrates the method for determining the color for a replacement tooth. This method for color determination can be carried out by a suitably equipped computer system, arranged with a scanner capable of scanning the colour of a tooth to be replaced T0.

In step 1201, the color of the (in this example) three regions A, B, C, is measured by use of the so-called CIE lab color standard (parameters L*, a*, b*, each with subscript index A, B or C).

In step 1202, an average $L_M$ of $L_A$, $L_B$, $L_C$ is determined, also an average $a_M$ of $a_A$, $a_B$, $a_C$ and an average $b_M$ of $b_A$, $b_B$, $b_C$ are determined, as arithmetic averages in this case.

Next in step 1203, the method determines the closest glass ceramic color determined ($L_g$, $a_g$, $b_g$) of the cap layer 41; 49, and the closest abutment core color ($L_{ac}$, $a_{ac}$, $b_{ac}$), wherein the following conditions must be satisfied ($L_g > L_{ac}$; $a_g > a_{ac}$; $b_g > b_{ac}$).

Then in step 1204, the glass ceramic local thickness $D_{ijk}$ is determined for each region A, B, C. For each region the unknown thickness $D_{ijk}$ is derived by solving the model using the measured CIE lab values for that region under assumption of a certain value of the opacity thickness $D_0$.

Then in step 1205, the abutment core coordinates i, j, k are calculated by subtracting an internally directed vector (i.e., in the direction from the surface into the interior of the restoration) with a length equal to the calculated $D_{ijk}$, from the surface coordinates x, y, z of the point were the digital color measurement took place. Where the vector ends, we find the adjusted coordinates of the abutment core.

The procedure ends in step 1206.

The description of the present invention will be illustrated below with some practical examples that relate to the various aspects of the present invention.

EXAMPLE 1

Zirconia Compound "PXA100P" of Tosoh Corporation, Tokyo, Japan is pre-mixed with 1000 ppm $Fe^{3+}$ for pigmentation to a tooth like shade. The mixture has a melting/injection temperature of 190-220° C. and is injection molded in a form which has a retractable part that forms an elliptical female recess to receive the male extension of the abutment core. The wax binder is removed by heating slowly to a temperature of about 450° C. and annealing at that temperature for about 3 hours in air. The implant is pre-sintered at about 800° C. for about 1 hour in air until neck forming has taken place to obtain a porous structure that is stable enough to be handled. The pre-sintered implant is fixed in a precisely vertical position in a dipping machine and submerged in a slurry consisting of a mixture of hydroxyapatite crystals and zirconia in a carrier liquid, containing dispersing agents and binders as four examples show in table 1.

Hydroxyapatite crystals of 20-50 nm diameter (Alfa-Aesar co., Ward Hill, Mass.) and yttria stabilized tetragonal zirconia polycrystals of 250-300 nm diameter (3Y-TZP, Tosoh, Co., Tokyo, Japan) in ethyl alcohol as a carrier liquid. An examples of such a slurries with the coating quality and the Simulated body Fluid (SBF) test results are given in the table 1.

TABLE 1

| Slurry component | Composition in weight percent | | | |
| --- | --- | --- | --- | --- |
| | No. 1 | No. 2 | No. 3 | No. 4 |
| Hydroxyapatite crystals, 20-50 nm | 55 | 25 | 35 | 5 |
| Y-TZP crystals, 250-300 nm | 10 | 40 | 30 | 60 |
| Total solids | 65 | 65 | 65 | 65 |
| Cyclohexanon | 2 | 2 | 2 | 2 |
| Ethyl alcohol | 29.5 | 29.5 | 29.5 | 29.5 |
| Disperbyk-190 | 1 | 1 | 1 | 1 |
| Dispersion | 97.5 | 97.5 | 97.5 | 97.5 |
| RM-8 | 2 | 2 | 2 | 2 |
| Polyvinyl Butyral B-9 | 0.5 | 0.5 | 0.5 | 0.5 |
| Binder content | 2.5 | 2.5 | 2.5 | 2.5 |
| Final slurry | 100 | 100 | 100 | 100 |

TABLE 1-continued

| | Composition in weight percent | | | |
|---|---|---|---|---|
| Slurry component | No. 1 | No. 2 | No. 3 | No. 4 |
| Results | | | | |
| Coating quality after membrane adsorption | Good Continuous | Good Continuous | Good Continuous | Good Continuous |
| Coating quality after sintering at 1350° C. | Cracked Loose | Continuous Integrated | Continuous Integrated | Continuous Integrated |
| Simulated Body Fluid test results, % of total area new apatite after 12 hrs | 85 | 100 | 100 | 10 |

The solid crystals are mixed with cyclohexanon, ethyl alcohol and Disperbyk-190 for 30 minutes in a tumbler. Then the RM-8 and PVB B-98 are added and left for 5 minutes on a roller bench. Then the mixture is ground with zirconia balls for 1 hour in a vibratory mill.

The implant is dipped and the slurry is deposited against the surface by absorption of the liquid carrier. Then the coated implants were sintered by heating in about 1 hour to about 800° C., about 2 hours to about 1000° C. and about 7 hours to about 1350° C., kept at that temperature for about 2 hours and then cooled down to room temperature by natural cooling. Finally the implants were soaked in a Simulated Body Fluid (SBF) at 36.5° C. for 12 hours. The SBF had the following composition: $K^+$ 5.0, $Na^+$ 142, $Mg^{2+}$ 1.5, $Ca^{2+}$, $Cl^-$ 103.8, $HCO_3^-$ 27.0, $HPO_4^{2-}$ 1.0, $SO_4^{2-}$ 0.5 mM. New nano-particles formed on the implant surface with a distinct morphology, where electron diffraction X-ray (EDX) patterns of apatite become distinct. The calcium phosphate gradually increases the Ca/P ratio up to 1.63, and eventually transforms into newly formed crystalline apatite, similar to the bone mineral. When 90% hydroxyapatite was used the coating did show cracking. In all other coatings was absent. However at 10% hydroxyapatite the bone forming with SBF was poor.

EXAMPLE 2

An impression is made of the arch to be implanted with a U-form non-opaque tray, filled with silicone, with three zirconia spheres attached in such a way that they are visible when the impression tray is in position. The silicone negative is poured in gypsum. The gypsum cast of the gypsum model is marked where the drill guide should end with black/white contrast for unambiguous scanning of the support area of the guide. Then a registration bite impression is made, while the patient bites in central occlusion. The patient is then scanned by X-ray Cone Beam Computed Tomography with the DVT 9000 of QR s.r.l., Verona (It). During scanning the impression tray with reference spheres is placed in the proper position in the patient mouth. After the CT scan and processing of the measurements, the operator checks whether all three reference spheres are visible in the X-ray image in three views to allow identification.

The next step in the automated fabrication of a drill guide and the aesthetic abutment or abutment crown is an optical impression obtained by laser scanning of the cast and the registration bite (see also: Van der Zel et al., The CICERO system for CAD/CAM fabrication of full-ceramic crowns. J Prosthet Dent 2001; 85:261-7). The CAD-CAM system makes use of a fast laser-stripe scanning method to measure the 3D geometry of the arch the opposing teeth. A straight laser stripe, which is projected onto the cast, is deformed by the 3D occlusal geometry of the tissues, and this deformation is used by the computer to determine the actual 3D positions of those points on the surface of the tissues. A charged coupled device (CCD) camera scans the projected line. The model is placed in the scanner clamping device, so that the path of insertion (2.6) of the drill guide (22) coincides approximately with the vertical z-axis of the scanner.

A rough overall-scan, using steps between consecutive scan lines of 0.2 mm, of the total arch which is to be implanted is made and converted to a 3D surface. In this relief, the location of the implant site, the approximal contacts of adjacent teeth and the extent of the scan area and the neighboring elements are entered. The incisal point, and a cusp tip on the last molar bilaterally are marked by clicking on the screen using the mouse. From this information the orientation of the occlusal plane in the masticatory system is defined and the scanner software generates a scanning protocol that prevents shadowed parts.

Then, the antagonist impression, placed on the model, is fine-scanned, using steps between consecutive scan lines of 0.05 mm, with a high definition. After removal from the cast, the cast with the implant site is subsequently scanned. Then the impression tray with the three reference spheres is placed on the model and the three spheres are scanned. The accuracy of the scanning method lies within 0.01 mm.

The registration bite data are merged with the CT-data in the CT Scan Space. The surgeon places the implant in the proper position, checking the end point position and the mucosa point of the implant position and the orientation of the implant with regard to the opposing teeth.

The design data of the implant drill holes and the scan data of the implant jaw are merged and reconstructed into a drill guide. The design data of the drill guide are converted to an SLA format (STL) and used to produce a drill guide by stereo lithography in a resin such as poly-methyl-methacrylate resin (PMMA).

After drilling the implant hole and placing of the implant, the patient is scanned in the same way as above by CT, to determine the position and the orientation of the female elliptical recess in the bioactive zirconia implant produced as in Example 1.

The design of the aesthetic abutment or abutment crown outer contour follows the following procedural steps: selection of proper element from the library, modelling the abutment or abutment crown on the screen to fit in with the remaining dentition and final adjustment of approximal contacts by the computer. A maxillary second pre-molar to be replaced by an implanted crown was designed on a the scanned implant with an abutment with a margin line that was adapted to the mucosa surrounding the implant location. The appropriate tooth is chosen by the operator from an extensive collection of generic forms of theoretical teeth in the program's library. When an intact mirror-element can be found in the arch, it can be scanned and used as a standard tooth. The distal and mesial contacts indicated by the operator in the occlusal and buccolingual views of the scan form the first step in the fitting of the generic tooth. The margin line of the new crown is adjusted to the mucosa line that was isolated automatically from the scan of the implant location.

The lingual and buccal boundaries are clicked in and dragged with the mouse, to shape the tooth so that it fits in a natural appearing row with the adjacent teeth. A warping algorithm generates a deformation field and deformation vectors within the field to generate the new form as directed by the drag vector indicated with the mouse. This way the external contours of the new crown can be adjusted interactively with the mouse, in much the same way of the building-up of porcelain by brush or spatula. After the crown has been fitted into the row, the computer adjusts the mesial and distal contacts to within +/−0.02 mm of the adjacent teeth The centric tooth-to-tooth contacts are obtained in relation to the quality of the opposing occlusal surface. Resulting contacts vary from a complex tri-podic occlusal situation in case of an ideal antagonist surface to a simple central contact on a less-defined occlusal surface.

The new crown is then superimposed on the opposing teeth which are displayed on the screen as a relief map. The CAD program deforms the generic tooth parametrically (with conservation of shape) according to gnathologic principles. On the library tooth preferred points of contact are used as anchor points to direct the search for contacts with the antagonist. The different fields of contacts of the crown are deformed to give maximal tooth-to-tooth contact with the opposing teeth. Because the theoretical tooth is brought into contact with antagonist as scanned, it can be assumed that contacts are also in the same range as the scanning accuracy, that is 0.01 mm.

The occlusal surface should allow cusps to escape and return to their fossae without interferences. Proper prosthetic fabrication should ensure that functional contact relationships are restored for both dynamic and static conditions. Maxillary and mandibular teeth should contact in a harmonious manner that allows optimum function, minimum trauma to the supporting structures, and an even distribution of load throughout the dentition. Positional stability of the occlusion is critical if implant integrity and proper function are to be maintained over time.

After the exterior tooth surfaces has been designed, several interface surfaces between the ceramic abutment core and between dentine and incisal porcelain are defined. The CAD-CAM software calculates the interior surface of the top topography of the pigmented zirconia abutment core. Taking the digital color map of the corresponding tooth the shade type of glass ceramic and the thickness of the shaded translucent layer, which determines the distance of the top side topographic surface from the designed outer contour of the aesthetic abutment crown, are calculated to in FIG. 12. by iterative linear interpolation between core color and nearest glass ceramic color until for L*, a* and b* for the top, middle and lower section of the abutment crown a distance D has been found. A distance of the abutment core from the outer contour surface of 0.7-0.8 mm was found as given in example 3.

A hexagon block of isostatically pressed or injection molded 3Y-TZP zirconia (Tosoh, Tokyo, Japan) was clamped on its two lateral sides in the prismatic clamping device in the milling machine. The underside of the abutment (6.3) was milled leaving it about 0.1 mm short of the mucosa line. The block is given a calibrated indentation for repositioning of the block in the longitudinal direction after sintering. The block is turned and the top side of the abutment is milled up to the mucosa line.

The block is sintered at about 1550° C., and experiences a shrinkage of about 19-25%. The block is repositioned laterally in the prismatic clamping device and the longitudinally position measured up by way of optical detection of the calibrated indention that was milled in the previous step in the unsintered block.

Veneering material is pressed over the abutment in the form of a paste of a glass ceramic having the same or a slightly lower linear thermal expansion coefficient as the zirconia-based abutment core. The properties of the materials used in this example are given in table 2.

TABLE 2

| Property | Y-TZPE Zirconia | Y-TZP Zirconia | Hydroxyl Ap/ZrO$_2$ | Glass ceramic |
|---|---|---|---|---|
| Application | Implant | Abutment | Coating | Veneer |
| Chemical composition in wt-%: | | | | |
| SiO$_2$ | — | — | — | 65 |
| ZrO$_2$ | 95 | 95 | 65 | — |
| Al$_2$O$_3$ | — | — | — | 16 |
| K$_2$O | — | — | — | 8 |
| Na$_2$O | — | — | — | 5 |
| CaO | — | — | — | 2 |
| Ca$_{10}$(PO$_4$)$_6$(OH)$_2$ | — | — | 35 | — |
| B$_2$O$_3$ | — | — | — | 1 |
| Li$_2$O | — | — | — | 1 |
| BaO | — | — | — | 1 |
| Y$_2$O$_3$ | 5 | 5 | — | 0.5 |
| Pigments | None | 1 mg/g Fe | None | 0.5 |
| Sinter temperature and hold time in ° C./min. | 1350/60 | 1550/30 | 1350/60 | 850/2 |
| Three-point bending strength in MPa | 1000 | 1000 | 200 | 100 |

About 120 g of the glass ceramic is mixed with 30 g of a 1.5 wt.-% Hydroxybutylcellulose (Methocel HB, Dow Chemical, USA) and 10 g distilled water. After overpressing the hexblock is dried for 4 hours at 80° C. in air. The veneering material is milled from the top but left short about 0.1 mm from the equator (6.9). The rim is finally milled away and the aesthetic abutment or abutment crown is sintered and finished. The aesthetic abutment crown is given a final polishing, and the veneered part is individualized by staining. Through a controlled model of the layering incisal and body porcelain esthetic effects, such as natural translucency and opalescence, can be obtained. The high-strength zirconia abutment core has been shaded to give a back-ground tone for the more translucent ceramic layers.

The last phase is a self-glazing step by heating to a temperature that lies 30 degrees under that of the incisal layer. A quick elevation to this temperature softens only the superficial layer and, therefore, enables creation of a superiorly glazed surface that reproduces the fine details without causing slumping. At the same time, the surface integrity that might have suffered from the grinding operation will be restored during this final glazing step. Polishing of the final restoration is not necessary because the glazing step is performed as a final treatment before the refractory is removed by grinding and air abrasion in the usual manner.

EXAMPLE 3

As an example: For the abutment core with a CIE-lab color: L*=73.6, a*=4.2, b*=19.4, a cover layer of with CIE-lab color: L*=70.6, a*=5.3, b*=21.2 with a thickness of 0.75 mm results at the outer surface in a CIE-lab color: L*=71.1, a*=5.1, b*=22.1, which corresponds with a traditionally measured VITA® lumen shade guide (Vita Zahnfabrik, DE) of "A3" (see also: Dozic, A; Kleverlaan, C J; Meegdes, M; vanderZel, J M; Feilzer A J, The influence of porcelain layer thickness on the final shade of ceramic restorations, J Prosth Dent 2003; 90:563-70).

EXAMPLE 4

The aesthetic abutment or abutment crown was designed as described in example 2. One method to build-up the top part of the abutment or abutment crown is 3D ink jet printing. In 3D jet printing a binder solution is used to fix the ceramic powder. First the design is converted into SLA-files, which slices the designed restoration in hundreds or more of two-dimensional cross-sections (FIG. 5a).

The procedure is as follows:

The printing machine spreads a layer of powder of dental material from the source piston to cover the surface of the build piston. A platen reversing relay allowed indefinite overprinting. The time delay between printing adjacent layers was controlled The resolution of the printer was 200×216 dpi. A modified version of the BIO.DOT microdoser (BIO.DOT Ltd., Huntington, Cambridshire, UK) was used for continuous ink jet printing. It has three main sections:

the ink control unit which contains ink jet printing and pressurizes ceramic ink using gas so that it flows, filters and recirculates the unit that creates, directs and prints droplets of ink, and the sliding table fitted with an optical track providing registration for automatic multi-layered printing.

The ceramic ink is pumped to the nozzle of 60 um diameter under a pressure of about 400 kPa through an in-line filter which contains a series of metal and polymeric filters of decreasing aperture. The stream formed at the nozzle was broken-up into small droplets by the pressure wave created by the piezoelectric drive rod at a frequency of 64 kHz. The droplets were charged simultaneously by the charging electrode having a voltage between 50-285 V. A detector in the charging electrode determined whether effective charging of droplets was achieved. Droplets with correct charge were deflected by the 18 kV high voltage plates. The uncharged droplets were not deflected but collected through the return tube placed directly below the main jet and pumped back into the reservoir. The droplets were visible through a window at the print head with the aid of LED illumination. The shape of the droplets were changed by controlling the modulation voltage.

The ink was dispersed using 2 wt. % of Hypermer KD1 (ICI Surfactants, Middlesborough, UK). The presence of 2 wt. % ammonium nitrate in a binary butylacetate-ethanol solvent mixture is used to produce conductive ink. Polyvinylbutyral and dibutyl sebacate serve as the binder and plasticizer, respectively.

The machine then prints binder solution containing concentrated pigments or colloidal size ceramic onto the loose powder, forming the first cross-section. The binder solution is passed through the printer nozzle which scanned each layer of ceramic particles formed into shape by roll compaction. The ceramic particles are dispersed and stabilized in inks and undispersed agglomerates can either be removed by sedimentation or be filtered out on-line just prior to printing, allowing a high density to be obtained in subsequent sintering. Ink composition can be changed at each print point allowing components with varied composition and microstructure to be produced with excellent resolution. Where the binder is printed, the powder is glued together and at the same way a 2D color print of pigment deposited. The remaining powder remains loose and supports the layers that will be printed above. It is also possible to used a laser printer and laser-sinter the powder together.

When the cross-section is complete, the build piston is lowered slightly, a new layer of powder is spread over its surface and the process is repeated.

The cover layer 41 grows layer by layer in the build piston until the part is completely surrounded and covered by loose powder.

Finally, the build piston is raised and the loose powder is vacuumed away, revealing the completed part.

This system is able to achieve an unrivaled build speed because the powder, which comprises the majority of the volume of he final restoration, is laid down quickly in bulk. The restoration has to be polished. After polishing the restoration has a natural appearance and the color that was designed.

EXAMPLE 5

Another method in comparison to example 4 is "robocasting". This is a slurry depositing technique capable of producing near-net-shaped restorations that utilizes feedstocks of negligible organic binder content (<1 vol.-%). The restoration was designed as described in example 2. In robocasting pseudoplastic suspensions (solids volume fraction ca. 0.50 are deposited onto a substrate, such as described in the first example: a milled and sintered abutment core still attached to the zirconia hexblock (6.4), in a precise pattern, according to an 2D surface. On minimal drying, the as-deposited suspension undergoes a liquid-to-solid transition that freezes-in the structure of the patterned restoration. The suspension is deposited in a precise pattern onto a moving X-Y table via computer aided design (CAD) instruction. The 3D restoration is constructed using a layer-by-layer build sequence. First the CAD-design of the cover layer 41 is converted into SLA-files, which slices the designed restoration in hundreds or more of two-dimensional cross-sections.

A glass ceramic powder (Example 2) was micronized for 4 hours in a vibratory ball mill. Darvan C (R.T. Vanderbilt Co), a 25% aqueous solution of ammonium polymethacrylate (APMA), was used as a dispersant in a quantity of 1.2 wt % of the porcelain. Partially hydrolyzed PVA (405S, Kuraray International Corp., Tokyo, Japan), with a degree of hydrolysis of 80.8 mol % and an average molecular weight of 28700 g/mol, was added. Tyzor TE (DuPont Chemicals, Deepwater, N.J.) was used as a crosslinking agent, because it reacts with PVA to form a gel. Tyzor TE contains 8.3 wt % titanium, and consists of a 25 wt % solution (in isopropylalcohol) of various organotitanate chelates. The pH was adjusted to 8.5 using $HNO_3$ or $NH_4OH$. The suspension was defoamed by addition of 0.25% 1-octanol by volume of solution and mixed for 2 h using a slow roll mill before casting. The cross-linking agent concentration was 0.0063 g of titanium/ml solution. The porcelain suspension and the cross-linking agent (Tyzor TE) solution were loaded into separate 30 ml polyethylene syringes. The system consists of a two-nozzle delivery system. The syringes were clamped to the SFF apparatus (CAMM3, Roland, Tokyo, Japan), each of which was fitted with a cooling coil that chilled the gel casting components to 15° C. to minimize chelation in the mixing chamber. The porcelain suspension and the cross-linking agent were pumped into the mixing chamber at a controlled ratio, homogenized using a paddle type mixer, extruded from the tip orifice, and deposited in a precise pattern onto The sintered zirconia hexblock on a moving X-Y table. Three-dimensional build-up was realized by stepwise increasing the Z-axis using a layer-by-layer build sequence. The X-Y-table, and thus the hexblock was heated to 30° C. to enhance gelation kinetics in the deposited layers. The restoration was dried in air and sintered at about 900° C. for 5 minutes under vacuum. The resulting restoration has a very natural appearance with colors as designed.

It is to be noted that the appearance description step is optional and that a prosthesis can be manufactured using a cap and making an impression in the traditional way.

Also, it is to be noted that the implant hole can have any form other shown in FIG. 4.

Similarly the prosthetic device can also be simplified as shown in FIG. 5b.

As will be apparent to one skilled in the art, different layering could also be used to imitate natural teeth color.

Of course, even though the above described apparatus and method have been described herein with respect to the production of a prosthetic could advantageously be measured via the apparatus of the present invention or using the method of the present invention.

As will be apparent to one skilled in the art, the color and translucency map output of an apparatus for measuring the color of the teeth in the mouth of the patient could be linked to a computer controlled milling apparatus that would mill a layer structure to duplicate the prosthetic device veneering shade according to this map.

This invention is not only concerned with ceramics. The same methods can be used with acrylic composite materials as a cover layer for the abutment.

Although the present invention has been described hereinabove by way of preferred embodiments thereof, it can be modified, without departing from the spirit and scope of the present invention as defined in the appended claims.

The invention claimed is:

1. A method for manufacturing a prosthesis for replacing at least one tooth, wherein the prosthesis is arranged for insertion in a patient's jawbone and the prosthesis comprises an implant and an abutment, wherein the abutment and the implant are arranged for placing the abutment on the implant; the method comprising the steps of:
    defining a shape of the prosthesis and a location in the jawbone for the prosthesis to be placed by using first image data of a first image taken by a CT scan (CT Scan I) of the patient's jawbone and by using second image data of a second image obtained from an optical scan of a gypsum cast, the gypsum cast taken from the patient's mouth,
wherein the method comprises the step of correlating the first image data and the second image data by:
    extracting from the first image data first reference marker data relating to a position of a first reference marker in the first image;
    extracting from the second image data second reference marker data relating to a position of a second reference marker in the second image, the second reference marker being the same as the first reference marker;
    retrieving from a second optical scan third image data of a third image taken from a registration bite for registration of a shape of an antagonist tooth, the tooth being antagonistic in relation to the location of the tooth to be replaced,
    merging the second reference marker data from the second image with the third image data,
    performing with use of the first and second reference marker data a geometric transformation operation on the second and third image data and/or the first image data to have a coincidence of the second and third image with the first image and to combine the first image data and the second and third image data into composite scan image data.

2. The method for manufacturing a prosthesis for replacing at least one tooth according to claim 1, wherein the first reference marker and the second reference marker are provided by an orientation device comprising at least three reference spheres located at defined distances from each other, the orientation device being in a reference position relative to the patient's jawbone during the first CT scan and during the taking of the gypsum cast and the imaging of the second image thereof; wherein the orientation device is fixed to an impression tray that is relatively translucent for CT scan radiation and the reference spheres are relatively opaque for CT scan radiation.

3. The method for manufacturing a prosthesis for replacing at least one tooth according to claim 2, wherein the orientation device is fixed to an impression tray for taking an impression of the patient's denture.

4. The method for manufacturing a prosthesis for replacing at least one tooth according to claim 1, wherein the second image data are data obtained from an optical scan of the gypsum cast.

5. The method for manufacturing a prosthesis for replacing at least one tooth according to claim 1, wherein the method comprises the steps of
    displaying the first image data and the second image data, and, from the displaying, obtaining information on a depth and an orientation being planned for the implant in the jawbone.

6. The method for manufacturing a prosthesis for replacing at least one tooth according to claim 5, wherein the method comprises the step of
    defining a shape of a drill guide from the first and second image data; the drill guide comprising a guiding hole and a drill tube, the drill tube being located in the guiding hole and arranged for holding, during use, a drill bit; the drill tube having an orientation for providing a drilling direction to coincide with the orientation for the implant and having a pre-calculated height for providing a depth transfer for the depth of the implant in the jawbone.

7. The method for manufacturing a prosthesis for replacing at least one tooth according to claim 6, wherein the method comprises the step of:
    removing undercuts of the shape of the drill guide in a direction of a path of insertion for the drill guide.

8. The method for manufacturing a prosthesis for replacing at least one tooth according to claim 5, wherein the method comprises the step of exporting image data of the shape of the drill guide to a production facility for manufacturing the drill guide by a stereo lithography manufacturing method (SLA) or rapid prototyping technique from a polymer material.

9. The method for manufacturing a prosthesis for replacing at least one tooth according to claim 1, wherein the method comprises the step of defining a shape of an abutment for the prosthesis from the first and the second image data, the abutment comprising an abutment body and a cap, the cap being arranged as cover of the abutment body.

10. The method for manufacturing a prosthesis for replacing at least one tooth according to claim 9, wherein the method further comprises the step of:
    defining an occlusal surface on the cap of the abutment by using the third image data.

11. The method for manufacturing a prosthesis for replacing at least one tooth according to claim 9, wherein the method comprises the step of exporting image data of the shape of the abutment to a production facility for manufacturing the abutment with the shape.

12. The method for manufacturing a prosthesis for replacing at least one tooth according to claim 11, wherein the abutment is made of a zirconia based ceramic.

13. The method for manufacturing a prosthesis for replacing at least one tooth according to claim 12, wherein the method comprises:
   forming a hexagon block of a yttria stabilized tetragonal zirconia polycrystalline (Y-TZP) zirconia;
   milling the lower side of the abutment body, leaving it about 0.1 mm short of a mucosal marginal line;
   milling a top side of the abutment body up to the marginal line, leaving a retention ridge all around;
   sintering at high temperatures of about 1550° C.;
   applying and pressing veneering material over the top side of the abutment;
   hardening or sintering the veneering material during a suitable heat treatment to form the cap of the abutment;
   milling the cap from the top and from the bottom leaving short about 0.1 mm from an equator of the cap, leaving a rim on the equator;
   milling away the rim on the equator.

14. The method for manufacturing a prosthesis for replacing at least one tooth according to claim 13, wherein the veneering material is applied in the form of a paste of a glass ceramic having the same or a slightly lower linear thermal expansion coefficient as the zirconia-based abutment core.

15. The method for manufacturing a prosthesis for replacing at least one tooth according to claim 1, wherein the method comprises the step of defining a shape of an implant for the prosthesis from the first and the second image data, wherein the implant comprises a structural body, a recess and a surface coating on an outer surface of the structural body.

16. The method for manufacturing a prosthesis for replacing at least one tooth according to claim 15, wherein the recess is arranged for receiving an extension of the abutment body for forming a connection between them.

17. The method for manufacturing a prosthesis for replacing at least one tooth according to claim 16, wherein the recess and the extension of the abutment body each has an ellipsoidal shape in cross-section.

18. The method for manufacturing a prosthesis for replacing at least one tooth according to claim 15, wherein the recess is arranged for receiving a healing stud.

19. The method for manufacturing a prosthesis for replacing at least one tooth according to claim 15, wherein the surface coating is arranged to provide a bioactive surface for advancing osseointegration after installation of the implant in the jawbone.

20. The method for manufacturing a prosthesis for replacing at least one tooth according to claim 19, wherein the surface coating comprises a mixture of zirconia and an apatite-compound.

21. The method for manufacturing a prosthesis for replacing at least one tooth according to claim 15, wherein the method comprises the step of exporting image data of the shape of the implant to a production facility for manufacturing the implant with the shape.

22. The method for manufacturing a prosthesis for replacing at least one tooth according to claim 21, wherein at least one of the abutment and the implant consists of a zirconia based ceramic.

23. The method for manufacturing a prosthesis for replacing at least one tooth according to claim 22, wherein the method comprises the steps of:
   forming an implant shape by injection molding of a zirconia based ceramic containing injection molding material;
   heating the implant shape slowly to a temperature of about 450° C. and annealing at that temperature in an air-comprising ambient;
   pre-sintering the implant shape at about 800° C. in air comprising ambient until neck forming to obtain a pre-sintered implant;
   dipping and submerging the pre-sintered implant in a slurry consisting of a mixture of apatite crystals and zirconia;
   sintering in steam saturated air for obtaining the implant.

24. A method for manufacturing a drill guide for use with the manufacturing of a prosthesis for replacing at least one tooth, wherein the prosthesis is arranged for insertion in a patient's jawbone and the prosthesis comprises an implant and an abutment, wherein the abutment and the implant are arranged for placing the abutment on the implant;
the method comprising the steps of:
   defining a shape of the prosthesis and a location in the jawbone for the prosthesis to be placed by using first image data of a first image taken by a CT scan (CT Scan I) of the patient's jawbone and by using second image data of a second image obtained from an optical scan of a gypsum cast, the gypsum cast taken from the patient's mouth,
wherein the method comprises the step of correlating the first image data and the second image data by:
   extracting from the first image data first reference marker data relating to a position of a first reference marker in the first image;
   extracting from the second image data second reference marker data relating to a position of a second reference marker in the second image, the second reference marker being the same as the first reference marker;
   retrieving from a second optical scan third image data of a third image taken from a registration bite for registration of a shape of an antagonist tooth, the tooth being antagonistic in relation to the location of the tooth to be replaced,
   merging the second reference marker data from the second image with the third image data,
      performing with use of the first and second reference marker data a geometric transformation operation on the second and third image data and/or the first image data to have a coincidence of the second and third image with the first image and to combine the first image data and the second and third image data into composite scan image data, and
   defining a shape for the drill guide from the first and second and third image data; the drill guide comprising a guiding hole and a drill tube, the drill tube being located in the guiding hole and arranged for holding, during use, a drill bit; the drill tube having an orientation for providing a drilling direction to coincide with an orientation for the implant and having a pre-calculated height for providing a depth transfer for a depth of the implant in the jawbone.

25. A method for manufacturing a prosthesis for replacing at least one tooth, wherein the prosthesis is arranged for insertion in a patient's jawbone and the prosthesis comprises an implant and an abutment, wherein the abutment and the implant are arranged for placing the abutment on the implant, wherein the method comprises the steps of
   taking a CT Scan (CT Scan I) of the patient's jawbone to obtain first image data of a first image, a first reference marker being provided during the CT Scan;

taking a gypsum cast from the patient's mouth;
taking an optical scan image of the gypsum cast to obtain second image data of a second image, a second reference marker being provided during the taking of the scan of the second image;
defining a shape of the prosthesis and a location in the jawbone for the prosthesis to be placed by using the first image data of the first image taken by a CT scan (CT Scan I) of the patient's jawbone and by using the second image data of the second image obtained from the optical scan of the gypsum cast, the gypsum cast taken from the patient's mouth,
correlating the first image data and the second image data by:
 extracting from the first image data first reference marker data relating to a position of the first reference marker in the first image;
 extracting from the second image data second reference marker data relating to a position of the second reference marker in the second image, the second reference marker being the same as the first reference marker;
 retrieving from a second optical scan third image data of a third image taken from a registration bite for registration of a shape of an antagonist tooth, the tooth being antagonistic in relation to the location of the tooth to be replaced,
 merging the second reference marker data from the second image with the third image data,
 performing with use of the first and second reference marker data a geometric transformation operation on the second and third image data and/or the first image data to have a coincidence of the second and third image with the first image and to combine the first image data and the second image data and third image data into composite scan image data.

26. A method for manufacturing and installing a prosthesis for replacing at least one tooth, wherein the prosthesis is arranged for insertion in a patient's jawbone and the prosthesis comprises an implant and an abutment, wherein the abutment and the implant are arranged for placing the abutment on the implant,
wherein the method comprises the steps of
taking a CT Scan (CT Scan I) of the patient's jawbone to obtain first image data of a first image, a first reference marker being provided during the CT Scan;
taking a gypsum cast from the patient's mouth;
taking an optical scan image of the gypsum cast to obtain second image data of a second image, a second reference marker being provided during the taking of the scan of the second image;
defining a shape of the prosthesis and a location in the jawbone for the prosthesis to be placed by using the first image data of the first image taken by a CT scan (CT Scan I) of the patient's jawbone and by using the second image data of the second image obtained from the optical scan of the gypsum cast, the gypsum cast taken from the patient's mouth,
correlating the first image data and the second image data by:
 extracting from the first image data first reference marker data relating to a position of the first reference marker in the first image;
 extracting from the second image data second reference marker data relating to a position of the second reference marker in the second image, the second reference marker being the same as the first reference marker;
 retrieving from a second optical scan third image data of a third image taken from a registration bite for registration of a shape of an antagonist tooth, the tooth being antagonistic in relation to the location of the tooth to be replaced,
 merging the second reference marker data from the second image with the third image data,
 performing with use of the first and second reference marker data a geometric transformation operation on the second and third image data and/or the first image data to have a coincidence of the second and third image with the first image and to combine the first image data and the second and third image data into composite scan image data.

27. A computer system for manufacturing a prosthesis for replacing at least one tooth, wherein the prosthesis is arranged for insertion in a patient's jawbone and the prosthesis comprises an implant and an abutment, wherein the abutment and the implant are arranged for placing the abutment on the implant;
wherein the computer system comprises a processing unit and memory, the memory being connected to the processing unit and being arranged for carrying out the steps of:
 defining a shape of the prosthesis and a location in the jawbone for the prosthesis to be placed by using first image data of a first image taken by a CT scan (CT Scan I) of the patient's jawbone and by using second image data of a second image obtained from an optical scan of a gypsum cast, the gypsum cast taken from the patient's mouth,
wherein the processing unit is arranged for carrying out the step of correlating the first image data and the second image data by:
 extracting from the first image data first reference marker data relating to a position of a first reference marker in the first image;
 extracting from the second image data second reference marker data relating to a position of a second reference marker in the second image, the second reference marker being the same as the first reference marker;
 retrieving from a second optical scan third image data of a third image taken from a registration bite for registration of a shape of an antagonist tooth, the tooth being antagonistic in relation to the location of the tooth to be replaced;
 merging the second reference marker data from the second image with the third image data:
  performing with use of the first and second reference marker data a geometric transformation operation on the second and third image data and/or the first image data to have a coincidence of the second and third image with the first image and to combine the first image data and the second and third image data into composite scan image data.

28. A computer program product to be loaded by a computer system for manufacturing a prosthesis for replacing at least one tooth, wherein the prosthesis is arranged for insertion in a patient's jawbone and the prosthesis comprises an implant and an abutment, wherein the abutment and the implant are arranged for placing the abutment on the implant;
wherein the computer system comprises a processing unit and memory, the memory being connected to the processing unit and being arranged for carrying out the steps of:

defining a shape of the prosthesis and a location in the jawbone for the prosthesis to be placed by using first image data of a first image taken by a CT scan (CT Scan I) of the patient's jawbone and by using second image data of a second image obtained from an optical scan of a gypsum cast, the gypsum cast taken from the patient's mouth, wherein the computer program product after being loaded allows the processing unit to carry out the step of correlating the first image data and the second image data by:

extracting from the first image data first reference marker data relating to a position of a first reference marker in the first image;

extracting from the second image data second reference marker data relating to a position of a second reference marker in the second image, the second reference marker being the same as the first reference marker;

retrieving from a second optical scan third image data of a third image taken from a registration bite for registration of a shape of an antagonist tooth, the tooth being antagonistic in relation to the location of the tooth to be replaced, merging the second reference marker data from the second image with the third image data, performing with use of the first and second reference marker data a geometric transformation operation on the second and third image data and/or the first image data to have a coincidence of the second and third image with the first image and to combine the first image data and the second and third image data into composite scan image data.

* * * * *